US008160202B2

(12) United States Patent
Hirooka et al.

(10) Patent No.: US 8,160,202 B2
(45) Date of Patent: Apr. 17, 2012

(54) RADIOGRAPHIC APPARATUS

(75) Inventors: Ken Hirooka, Kyoto (JP); Shouji Kuwabara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 176 days.

(21) Appl. No.: 12/765,373

(22) Filed: Apr. 22, 2010

(65) Prior Publication Data

US 2010/0272236 A1    Oct. 28, 2010

(30) Foreign Application Priority Data

Apr. 28, 2009    (JP) ................................ 2009-109229

(51) Int. Cl.
*G01N 23/04*    (2006.01)
*G21K 1/02*    (2006.01)

(52) U.S. Cl. ......................................... 378/62; 378/154

(58) Field of Classification Search .................... 378/62, 378/154, 137; 382/131, 132
See application file for complete search history.

(56) References Cited

U.S. PATENT DOCUMENTS

2002/0168052 A1 *  11/2002  Castleberry ................... 378/154
2009/0016494 A1 *   1/2009  Jans et al. ..................... 378/154

FOREIGN PATENT DOCUMENTS

JP    2002-257939 A    9/2002

* cited by examiner

*Primary Examiner* — Irakli Kiknadze
(74) *Attorney, Agent, or Firm* — Cheng Law Group, PLLC

(57) ABSTRACT

A radiographic apparatus includes a radiation source for emitting radiation, a radiation detecting device with detecting elements arranged two-dimensionally, a radiation grid with absorbing foil strips for removing scattered radiation, a physical quantity acquiring device for calculating predetermined physical quantities based on outputs of the radiation detecting device, a physical quantity map generating device for generating a physical quantity map by mapping the predetermined physical quantities, and a physical quantity map smoothing device for smoothing the physical quantities arranged on the physical quantity map in a direction of extension of the absorbing foil strips, thereby to generate an average value map.

20 Claims, 10 Drawing Sheets

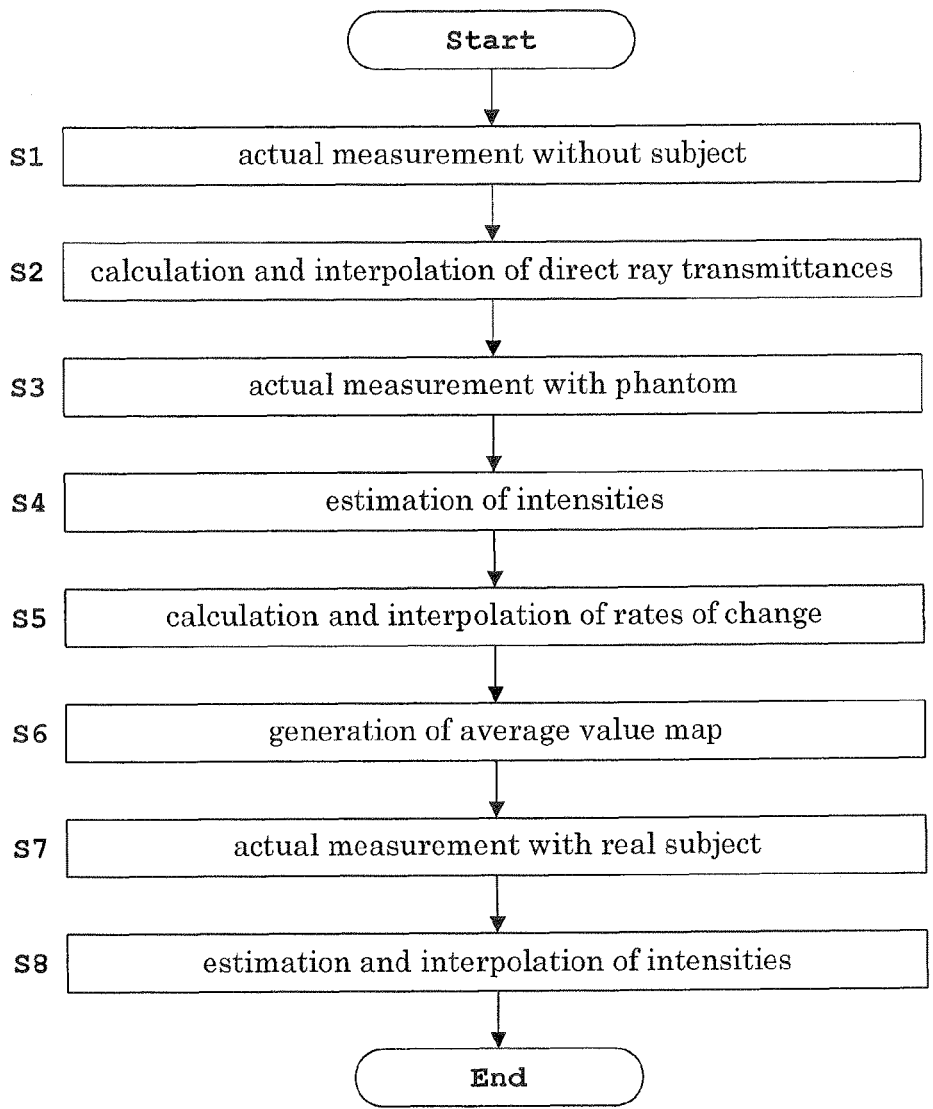
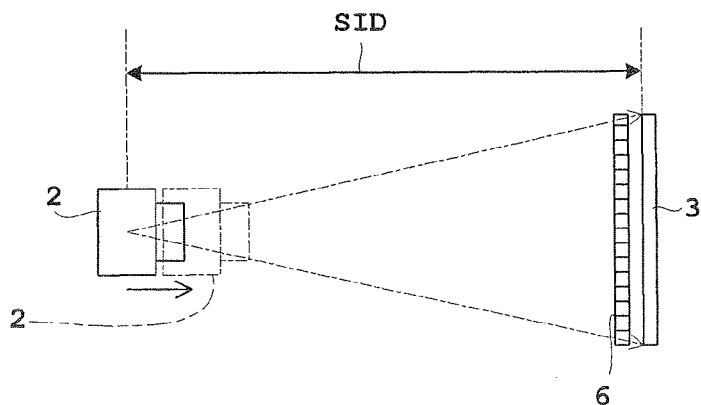

Fig. 9
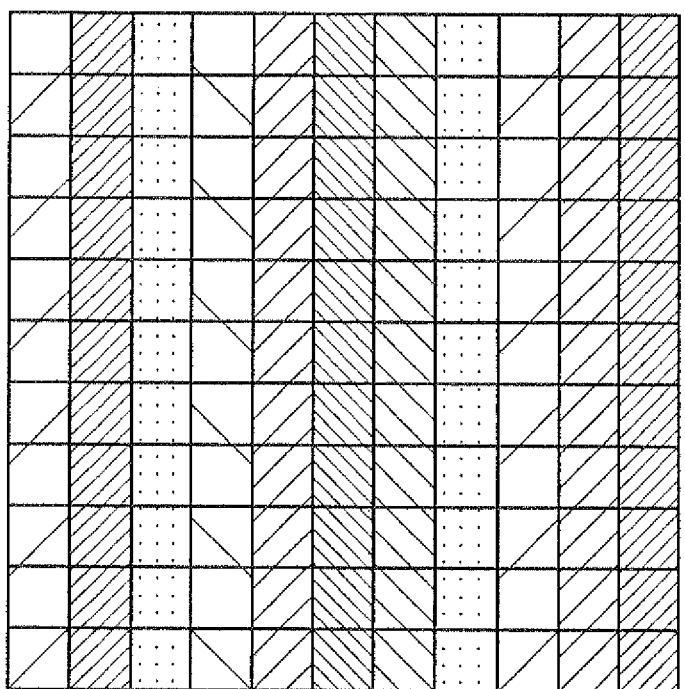
M1
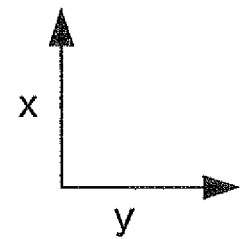

Fig.11A
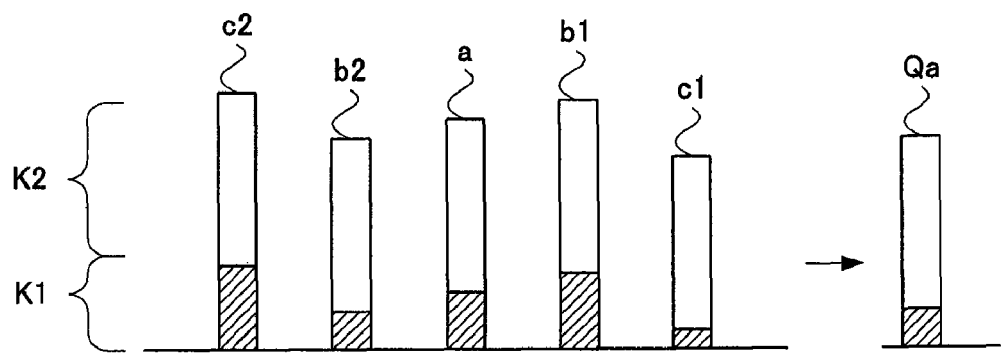
Fig.11B
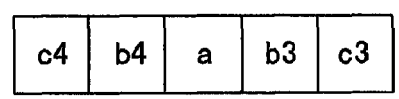
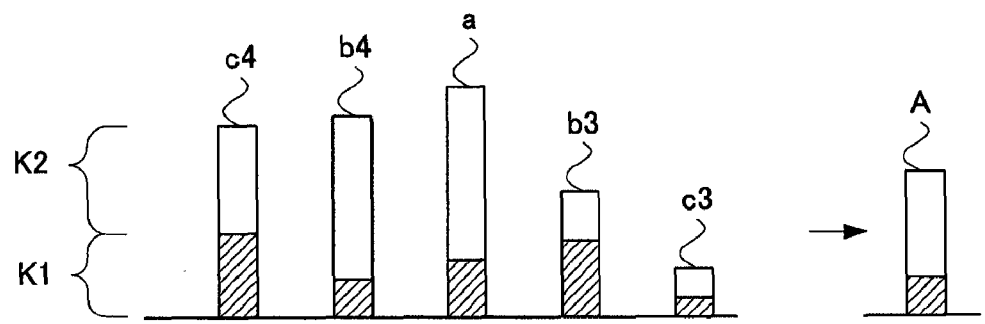

RADIOGRAPHIC APPARATUS

BACKGROUND OF THE INVENTION (1) Field of the Invention

This invention relates to a radiographic apparatus for picking up fluoroscopic images of a subject, and more particularly to a radiographic apparatus having a radiation grid for removing scattered radiation occurring when radiation passes through the subject.

(2) Description of the Related Art

Conventionally, in order to prevent scattered X-rays (hereinafter called simply "scattered rays") transmitted through a subject or patient from entering an X-ray detector, a medical X-ray fluoroscopic apparatus or X-ray CT (computed tomography) uses a grid (scattered radiation removing device) for removing the scattered rays. However, even if the grid is used, a false image is produced by the scattered rays passing through the grid, and a false image by absorbing foil strips constituting the grid. Particularly where a flat panel (two-dimensional) X-ray detector (FPD: Flat Panel Detector) with detecting elements arranged in a matrix form (two-dimensional matrix form) is used as the X-ray detector, a false image such as a moire pattern is produced due to a difference between the spacing of the absorbing foil strips of the grid and the pixel spacing of the FPD, besides the false image by the scattered rays. In order to reduce such false images, a false image correction is needed. In order not to produce such a moire pattern, a synchronous grid has been proposed recently, which grid has absorbing foil strips arranged parallel to either the rows or the columns of the detecting elements, and in number corresponding to an integral multiple of the pixel spacing of the FPD, and a correction method for use of this grid is also needed (see Japanese Unexamined Patent Publication No. 2002-257939, for example).

By way of correcting moire patterns, a method of image processing which includes smoothing, for example, is carried out nowadays. When false image correction is done to excess, the resolution of direct X-rays (hereinafter called simply "direct rays") also tends to lower. Therefore, an attempt to reduce false images reliably through image processing will lower the resolution of direct rays, resulting in less clear patient images. Conversely, when greater importance is placed on the resolution of direct rays to obtain clear patient images, the false images will not be reduced through image processing, which constitutes what is called a trade-off between image processing and clearness. Thus, a perfect false image processing is difficult. Regarding the correction of the scattered rays remaining despite use of a grid, various methods have been proposed but these have disadvantages such as involving a time-consuming correcting arithmetic operation.

In connection with the correction method for use of a synchronous grid, Applicant herein has already proposed a method in which correction is carried out with respect to pixels shielded from direct rays by the absorbing foil strips, a distribution of scattered rays having passed through the grid is derived from the columns or rows of the shielded pixels, and signals of the other pixels are corrected based on the distribution. It has been proposed in the above method to set the distance between the grid and X-ray detector to an integral multiple of the height of the absorbing foil strips, and to set the position of the grid and the shape of the absorbing foil strips such that shadows of the absorbing foil strips fall only on certain pixel columns or pixel rows despite changes in the positions of a radiation emitting device such as an X-ray tube, the grid and the X-ray detector.

However, such conventional constructions have the following drawbacks.

When passing through the grid, most of the scattered rays are absorbed but parts thereof leave the grid without being absorbed. The manner of this passage is varied in different portions of the detecting plane of the X-ray detector, under the influence of a distortion in the arrangement of the absorbing foil strips. Specifically, the manner of passage of the scattered rays will be reflected on the X-ray detector. Thus, the influence of the scattered rays spreads over the entire X-ray detector.

In order to eliminate this influence, a pattern (striped pattern of the scattered rays) that appears in a patient image due to the manner of passage of the scattered rays being varied in different portions the X-ray detector may be stored beforehand as a rate of change map. This striped pattern of the scattered rays may be removed through the above image processing.

However, noise (statistical noise) not influenced by the scattered rays is superimposed on the above rate of change map. The striped pattern of the scattered rays is greatly changeable with the manner of distortion of the absorbing foil strips, and therefore its prediction is difficult. Thus, the rate of change map is acquired by actually applying X-rays to the X-ray detector with the grid attached thereto. At this time, there is no guarantee that the dose of X-rays reaching the detecting elements is the same for all the detecting elements, but certain variations will take place. These variations are superimposed on the rate of change map, causing the statistical noise. These variations occur also when the grid is not attached to the X-ray detector, and are independent of the above striped pattern of scattered rays.

To put it simply, the image processing for removing the striped pattern of scattered rays is carried out by placing the rate of change map on a fluoroscopic image. The statistical noise is superimposed on the rate of change map, apart from the striped pattern of scattered rays. When the rate of change map is applied to the image, pixel values of the image will be changed excessively by an amount corresponding to the statistical noise superimposed on the rate of change map. This causes granular noise to appear on the image.

SUMMARY OF THE INVENTION

This invention has been made having regard to the state of the art noted above, and its object is to provide a radiographic apparatus which does not superimpose the influence of statistical noise on images.

The above object is fulfilled, according to this invention, by a radiographic apparatus for obtaining a radiographic image, comprising a radiation source for emitting radiation; a radiation detecting device having a plurality of detecting elements arranged two-dimensionally in rows and columns for detecting the radiation; a radiation grid with absorbing foil strips extending in a direction of the rows and arranged in a direction of the columns for removing scattered radiation; a physical quantity acquiring device for calculating predetermined physical quantities to determine pixel values of pixels arranged two-dimensionally; a physical quantity map generating device for generating a physical quantity map by mapping the predetermined physical quantities; and a physical quantity map smoothing device for smoothing the physical quantities arranged on the physical quantity map in the direction of extension of the absorbing foil strips, thereby to generate an average value map.

According to this invention, the physical quantity map generating device is provided for generating a physical quantity map. This physical quantity map shows a pattern (striped pattern of scattered radiation) to appear on a fluoroscopic image. The striped pattern of scattered radiation will be removed by correcting the fluoroscopic image using this map. The above construction includes the physical quantity map smoothing device for smoothing this physical quantity map to generate an average value map. The physical quantity map has, superimposed thereon, statistical noise besides the striped pattern of scattered radiation. However, the physical quantity map is smoothed to become the average value map. On the average value map, the statistical noise is averaged and blurred. Even if the statistical noise tends to be reflected as granular coarse false images on the fluoroscopic image, its granularity is blurred on the average value map. Consequently, the statistical noise on the physical quantity map is never superimposed on the fluoroscopic image.

The smoothing is carried out for the physical quantities arranged in a line along the direction of extension of the absorbing foil strips of the radiation grid. Desirably, the striped pattern of scattered radiation is not blurred by the smoothing. The striped pattern of scattered radiation extends along the direction of extension of the absorbing foil strips of the radiation grid (in other words, the striped pattern of scattered radiation is arranged along the direction of arrangement of the absorbing foil strips of the radiation grid). Since the smoothing is carried out along the direction of extension of the absorbing foil strips of the radiation grid, components of the statistical noise included in the physical quantities are smoothed, but components of the striped pattern of scattered radiation are not. Consequently, the striped pattern of scattered radiation appearing on the physical quantity map is not blurred by the smoothing, and the pattern can be removed without appearing on the fluoroscopic image.

Preferably, the above radiographic apparatus further comprises a pixel specifying device for specifying certain pixels among pixels forming the radiographic image; and an intensity estimating device for estimating at least one of scattered radiation intensity at the certain pixels specified by the pixel specifying device, and direct radiation intensity at the certain pixels; wherein (A) a rate of change calculating device is provided as a component corresponding to the physical quantity acquiring device, for determining a rate of change for each pixel relative to an average value or a value of each pixel obtained by smoothing and interpolating calculations as a reference intensity for all the pixels relating to the radiation intensity, using the radiation intensity estimated by the intensity estimating device based on actual measurement carried out in the presence of a subject; (B) a rate of change map generating device is provided as a component corresponding to the physical quantity map generating device, for generating a rate of change map by mapping the rate of change for each pixel; and (C) a rate of change map smoothing device is provided as a component corresponding to the physical quantity map smoothing device, for smoothing rates of changes arranged on the rate of change map in the direction of extension of the absorbing foil strips, thereby to generate the average value map.

The above construction represents a specific embodiment of the radiographic apparatus according to this invention. That is, the above construction includes the rate of change map generating device for generating a rate of change map. This rate of change map shows a pattern (striped pattern of scattered radiation) appearing on a fluoroscopic image. The striped pattern of scattered radiation will be removed by correcting the fluoroscopic image using this map. The above construction includes the rate of change map smoothing device for smoothing this rate of change map to generate an average value map. The rate of change map has, superimposed thereon, statistical noise besides the striped pattern of scattered radiation. However, the rate of change map is smoothed to become the average value map. On the average value map, the statistical noise is averaged and blurred. Even if the statistical noise tends to be reflected as granular coarse false images on the fluoroscopic image, its granularity is blurred on the average value map. Consequently, the statistical noise on the rate of change map is never superimposed on the fluoroscopic image.

The smoothing is carried out for the rates of change arranged in a line along the direction of extension of the absorbing foil strips of the radiation grid. Desirably, the striped pattern of scattered radiation is not blurred by the smoothing. The striped pattern of scattered radiation extends along the direction of extension of the absorbing foil strips of the radiation grid (in other words, the striped pattern of scattered radiation is arranged along the direction of arrangement of the absorbing foil strips of the radiation grid). Since the smoothing is carried out along the direction of extension of the absorbing foil strips of the radiation grid, components of the statistical noise included in the rates of change are smoothed, but components of the striped pattern of scattered radiation are not. Consequently, the striped pattern of scattered radiation appearing on the rate of change map is not blurred by the smoothing, and the pattern can be removed without appearing on the fluoroscopic image.

In the above radiographic apparatus, it is preferred that the intensity estimating device is arranged to estimate radiation intensity at the certain pixels specified by the pixel specifying device, based on the average value map, direct radiation transmittance calculated by the transmittance calculating device, and actual measurement intensity which is a radiation intensity after transmission through the scattered radiation removing device in actual measurement carried out in the presence of a different subject.

A specific construction for reflecting this is as follows. The radiation source emits radiation in the presence of a different subject (i.e. a subject used in actual radiography here) to be incident on the radiation detecting device through the radiation removing device, thereby to obtain actual measurement intensity which is radiation intensity after transmission through the radiation removing device in actual measurement in the presence of the subject. Based on the rates of change calculated by the rate of change calculating device, the direct radiation transmittances calculated by the transmittance calculating device, and the actual measurement intensity in the actual measurement in the presence of the different subject (i.e. the subject used in actual radiography), the intensity estimating device estimates radiation intensity at the certain pixels specified by the pixel specifying device. Thus, direct radiation transmittance is obtained based on the actual measurement data taken in the absence of a subject. Using the direct radiation transmittance, rates of change are obtained by, carrying out radiography in the presence of a subject (i.e. the phantom). Using the rates of change or the rates of change interpolated by the rate of change interpolating device, radiation intensity can be estimated based on the actual measurement intensity obtained from radiography carried out in the presence of the different subject (i.e. the subject used in actual radiography).

In the above radiographic apparatus, it is preferred that the physical quantity map smoothing device is arranged to remove influences of statistical noise superimposed on the physical quantity map.

The above construction makes clear the meaning of providing the physical quantity map smoothing device. If the statistical noise superimposed on the physical quantity map is removed, no false image will appear on the image depicting the subject.

In the above radiographic apparatus, it is preferred that spacing between the absorbing foil strips of the radiation grid adjoining in the direction of the columns is synchronized with an integral multiple of spacing between the detecting elements of the radiation detecting device adjoining in the direction of the columns.

The above shows a specific construction of the radiographic apparatus according to this invention. If spacing in the arrangement of the absorbing foil strips is set with reference to the arrangement of the detecting elements, when radiation is emitted from the radiation source, there will be no interference between an arrangement of shadows of the absorbing foil strips reflected on the radiation detection device and the arrangement of the detecting elements to produce a moire on the image.

Preferably, the above radiographic apparatus further comprises a C-arm for supporting the radiation source and the radiation detecting device.

The above shows a specific construction of the radiographic apparatus according to this invention. This invention is adaptable to a common radiographic apparatus having a C-arm.

According to this invention, as described above, a radiographic image is obtained appropriately based on radiation intensity. A radiographic image of only direct radiation is obtained with shadows of the scattered radiation removing device eliminated and scattered radiation removed completely. A proper radiographic image can be obtained without depending on the scattered radiation removing device.

According to this invention, the physical quantity map generating device is provided for generating the physical quantity map. And the physical quantity map smoothing device is provided for smoothing this physical quantity map to generate the average value map. The physical quantity map is smoothed to become the average value map. On the average value map, statistical noise is averaged and blurred. Consequently, the statistical noise on the physical quantity map is never superimposed on a fluoroscopic image.

The smoothing is carried out for the rates of change arranged in a line along the direction of extension of the absorbing foil strips of the radiation grid. Then, components of the statistical noise included in the rates of change on the physical quantity map are smoothed, but components of the striped pattern are not. Consequently, the striped pattern of scattered radiation appearing on the physical quantity map is not blurred by the smoothing, thereby removing the pattern otherwise appearing on the fluoroscopic image.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 5 is a flow chart showing a sequence of X-ray imaging according to Embodiment 1;

FIG. 6 is a schematic view of X-ray imaging without a subject;

FIG. 9 is a schematic view illustrating a rate of change map according to Embodiment 1;

FIG. 11A is a schematic view illustrating the effect of smoothing according to the construction in Embodiment 1;

FIG. 11B is a schematic view illustrating the effect of smoothing according to the construction in Embodiment 1;

DESCRIPTION OF THE PREFERRED EMBODIMENTS

A preferred embodiment of this invention will be described hereinafter with reference to the drawings.

Embodiment 1

Figure 1:
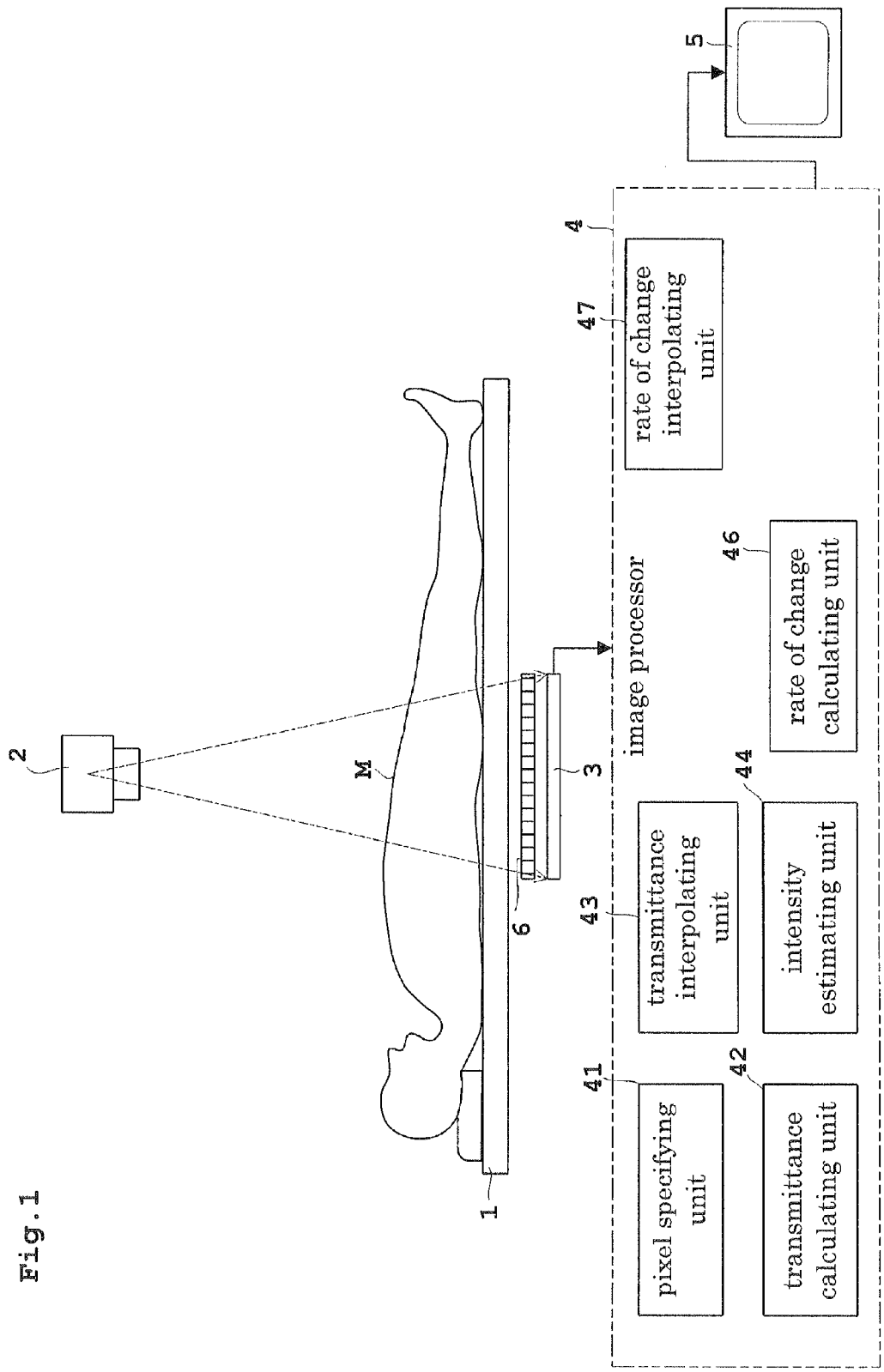
FIG. 1 is a block diagram of an X-ray apparatus according to Embodiment 1.
Figure 2:
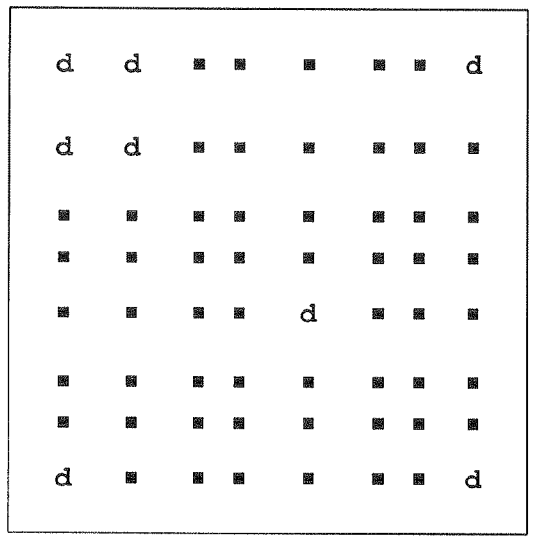
FIG. 2 is a schematic view of a detecting plane of a flat panel X-ray detector (FPD)
Figure 3:
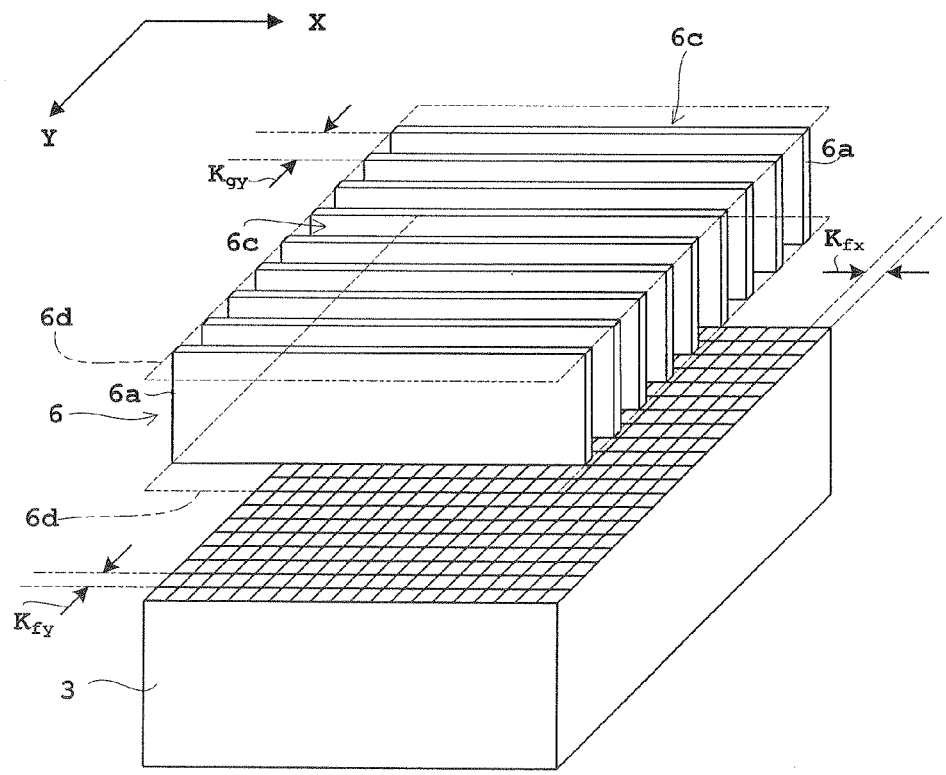
FIG. 3 is a schematic view of a grid.

FIG. 1 is a block diagram of an X-ray imaging apparatus according to Embodiment 1. FIG. 2 is a schematic view of a detecting plane of a flat panel X-ray detector (FPD). FIG. 3 is a schematic view of an X-ray grid. Embodiment 1 will be described taking X-rays as an example of radiation.

As shown in FIG. 1, the X-ray apparatus according to Embodiment 1 includes a top board 1 for supporting a subject M, an X-ray tube 2 for emitting X-rays toward the subject M, a flat panel X-ray detector (hereinafter abbreviated as "FPD") 3 for detecting the X-rays emitted from the X-ray tube 2 and transmitted through the subject M, an image processor 4 for carrying out image processes based on the X-rays detected by the FPD 3, and a display 5 for displaying X-ray images having undergone the image processes by the image processor 4. The display 5 is in the form of a display device such as a monitor, television or the like. A grid 6 is attached to the detecting plane of the FPD 3. The X-ray tube 2 corresponds to the radiation emitting device in this invention. The flat panel X-ray detector (FPD) 3 corresponds to the radiation detecting device in this invention. The grid 6 corresponds to the scattered radiation removing device in this invention.

The image processor 4 includes a central processing unit (CPU) and others. The programs and the like for carrying out various image processes are written and stored in a storage medium represented by a ROM (Read-only Memory). The CPU of the image processor 4 reads from the storage medium and executes the programs and the like to carry out image processes corresponding to the programs. In particular, a pixel specifying unit 41, a transmittance calculating unit 42, a transmittance interpolating unit 43, an intensity estimating unit 44, a rate of change calculating unit 46 and a rate of change interpolating unit 47, described hereinafter, of the image processor 4 execute a program relating to specification of certain predetermined pixels, calculation and interpolation of direct ray transmittances, intensity estimation and interpolation, and calculation of rates of change, on the basis of detection signals outputted from the FPD 3. In this way, the above components carry out specification of the certain pixels, calculation and interpolation of the direct ray transmittances, intensity estimation and interpolation, and calculation of the rates of change, corresponding to the program, respectively.

The image processor 4 includes the pixel specifying unit 41 for specifying certain predetermined pixels, the transmittance calculating unit 42 for calculating direct ray transmittances, the transmittance interpolating unit 43 for interpolating the direct ray transmittances, the intensity estimating unit 44 for estimating intensities, the rate of change calculating unit 46 for calculating rates of change, and the rate of change interpolating unit 47 for interpolating the rates of change. The image processor 4 further includes a rate of change map generating unit 48 and a smoothing unit 49, which will be described in detail hereinafter. The pixel specifying unit 41 corresponds to the pixel specifying device in this invention. The transmittance calculating unit 42 corresponds to the transmittance calculating device in this invention. The transmittance interpolating unit 43 corresponds to the transmittance interpolating device in this invention. The intensity estimating unit 44 corresponds to the intensity estimating device in this invention. The rate of change calculating unit 46 corresponds to the rate of change calculating device in this invention. The rate of change interpolating unit 47 corresponds to the rate of change interpolating device in this invention. The rate of change map generating unit 48 corresponds to the rate of change map generating device in this invention. The smoothing unit 49 corresponds to the rate of change map smoothing device in this invention.

As shown in FIG. 2, the FPD 3 has a plurality of detecting elements d sensitive to X-rays arranged in a two-dimensional matrix form on the detecting plane thereof. The detecting elements d detect X-rays by converting the X-rays transmitted through the subject M into electric signals to be stored once, and reading the electric signals stored. The electric signal detected by each detecting element d is converted into a pixel value corresponding to the electric signal. An X-ray image is outputted by allotting the pixel values to pixels corresponding to positions of the detecting elements d. The X-ray image is fed to the pixel specifying unit 41, transmittance calculating unit 42 and intensity estimating unit 44 of the image processor 4 (see FIGS. 1 and 4). Thus, the FPD 3 has the plurality of detecting elements d arranged in a matrix form (two-dimensional matrix form) for detecting X-rays. The detecting elements d correspond to the detecting elements in this invention.

As shown in FIG. 3, the grid 6 has, arranged alternately, absorbing foil strips 6a for absorbing scattered rays (scattered X-rays), and intermediate layers 6c for transmitting scattered rays through. The absorbing foil strips 6a and intermediate layers 6c are covered by grid covers 6d located on an X-ray incidence plane and on an opposite plane with the absorbing foil strips 6a and intermediate layers 6c in between. In order to clarify illustration of the absorbing foil strips 6a, the grid covers 6d are shown in two-dot chain lines, and other details of the grid 6 (e.g. a structure for supporting the absorbing foil strips 6a) are not shown. The absorbing foil strips 6a correspond to the absorbing layers in this invention.

Next, the arrangement of absorbing foil strips 6a will be described. Specifically, the absorbing foil strips 6a and intermediate layers 6c extending along the X-direction in FIG. 3 are arranged alternately in order in the Y-direction in FIG. 3. The X-direction in FIG. 3 is parallel to the rows of detecting elements d of the FPD 3 (see FIG. 2), and the Y-direction in FIG. 3 is parallel to the columns of detecting elements d of the FPD 3 (see FIG. 2). Therefore, in Embodiment 1, the direction of arrangement of absorbing foil strips 6a is parallel to the rows of detecting elements d.

Spacing $K_{gy}$ between the absorbing foil strips 6a adjoining in the Y-direction is synchronized with an integral multiple (shown to be double in FIG. 3) of spacing $K_{fy}$ between adjoining pixels (detecting elements d). Thus, the grid 6 is constructed such that the direction of arrangement of absorbing foil strips 6a is parallel to the rows of detecting elements d, and that the spacing $K_{gy}$ between adjacent absorbing foil strips 6a is an integral multiple of spacing $K_{fy}$ between adjacent pixels.

In Embodiment 1, the intermediate layers 6c are void. Therefore, the grid 6 is also an air grid. The absorbing foil strips 6a are not limited to any particular material, as long as a material such as lead is used which absorbs radiation represented by X-rays. As the intermediate layers 6c, instead of being void as noted above, any intermediate material such as aluminum or organic substance may be used which transmits radiation represented by X-rays.

Figure 4:
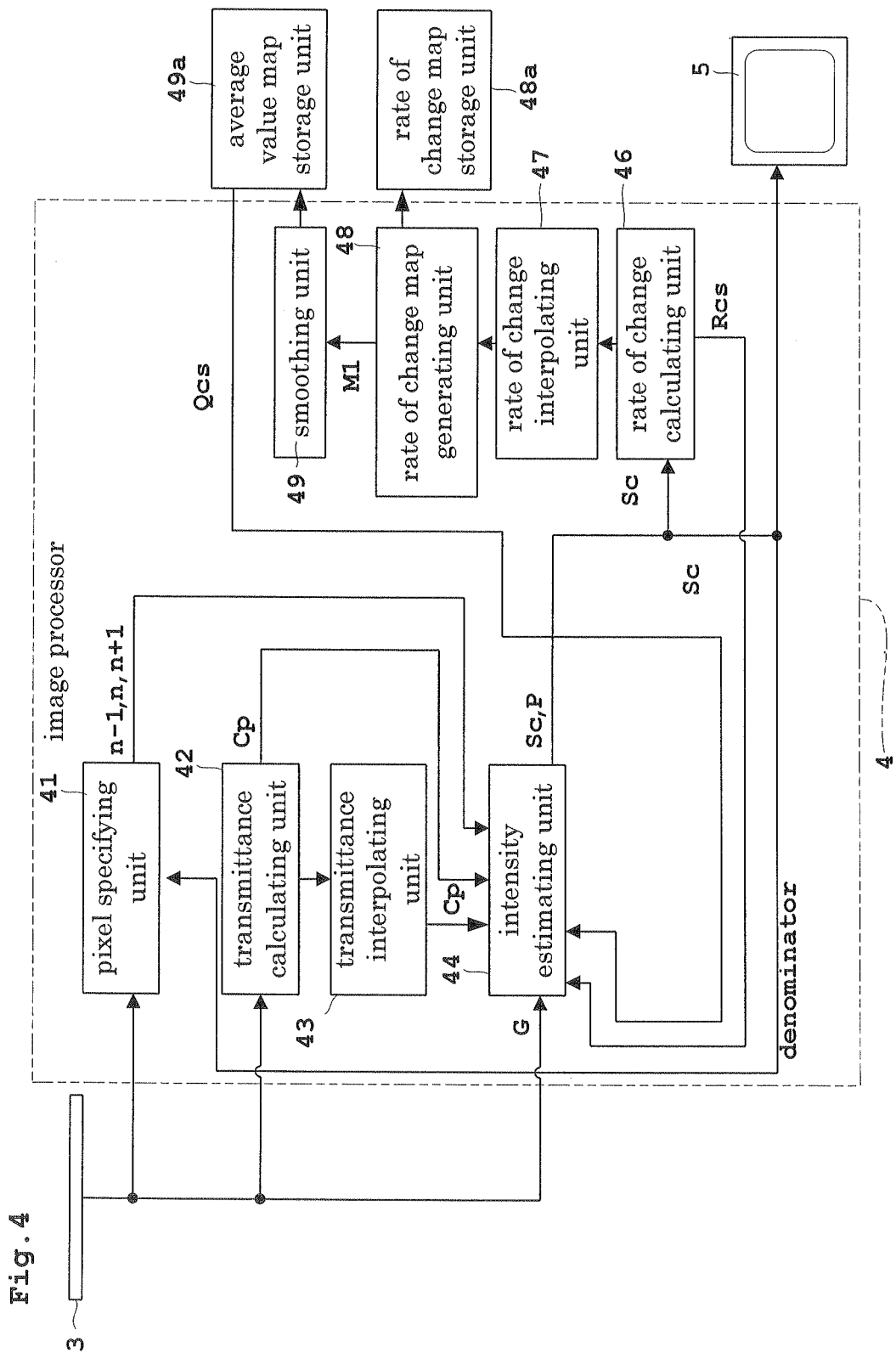
FIG. 4 is a block diagram showing a specific construction of an image processor and data flows according to Embodiment 1.
Figure 7:
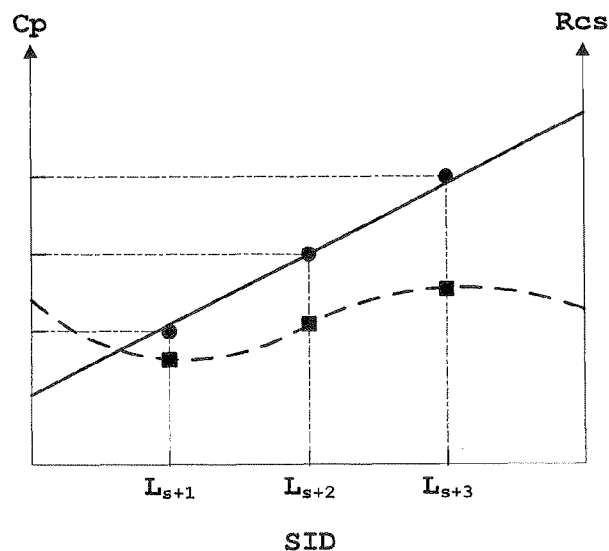
FIG. 7 is a graph schematically showing a relationship between SID, direct ray transmittance and rate of change.
Figure 8:
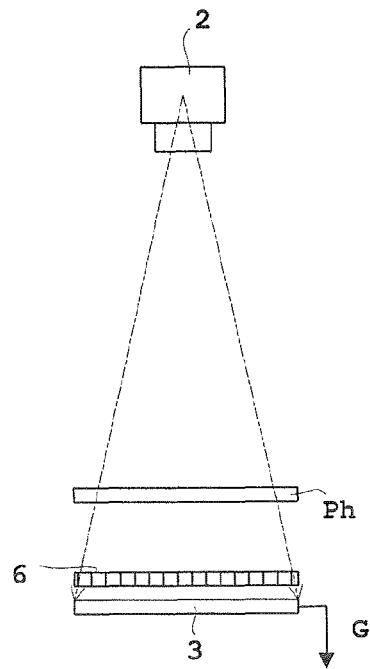
FIG. 8 is a view schematically showing X-ray imaging in the presence of a subject according to Embodiment 1, using a phantom in the form of an acrylic plate as the subject.

An actual X-ray imaging and data flows according to Embodiment 1 will be described with reference to FIGS. 4 through 8. FIG. 4 is a block diagram showing a specific construction of the image processor 4 and data flows. FIG. 5 is a flow chart showing a sequence of X-ray imaging according to Embodiment 1. FIG. 6 is a schematic view of X-ray imaging without a subject. FIG. 7 is a graph schematically showing a relationship between SID, direct ray transmittance and rate of change. FIG. 8 is a view schematically showing X-ray imaging in the presence of a subject according to Embodiment 1, using a phantom in the form of an acrylic plate as the subject.

As shown in FIG. 4, the pixel specifying unit 41 specifies certain pixels among the pixels forming an X-ray image. In Embodiment 1, the pixel specifying unit 41 specifies a combination of three pixels consisting of an (n−1)th pixel, an adjoining, nth pixel and a next adjoining, (n+1)th pixel (indicated "n−1", "n" and "n+1" in FIG. 4), and feeds the combination to the intensity estimating unit 44. When the absolute value of the denominator included in the solution of simultaneous equations described hereinafter has a predetermined value or less (the denominator being "0" in Embodiment 1), the pixel specifying unit 41 does not select the pixels forming the combination for the simultaneous equations, but selects and specifies other pixels for the combination. Since the simultaneous equations are derived from the intensity estimating unit 44 as is clear from the description made hereinafter, data relating to the denominator (indicated "denominator" in FIG. 4) derived from the intensity estimating unit 44 is fed to the pixel specifying unit 41.

The transmittance calculating unit 42 determines, in relation to discrete distances between the X-ray tube 2 and the grid 6/FPD 3, direct ray transmittances which reflect direct rays (direct X-rays) before transmission and after transmission through the grid 6 obtained from actual measurements taken in the absence of a subject. In Embodiment 1, the transmittance calculating unit 42 calculates the direct ray transmittances (indicated "Cp" in FIG. 4), and feeds the transmittances to the transmittance interpolating unit 43 and intensity estimating unit 44.

The transmittance interpolating unit 43 interpolates the direct ray transmittances Cp calculated by the transmittance calculating unit 42 in distances around the above discrete distances. The interpolated direct ray transmittances Cp also are fed to the intensity estimating unit 44.

The intensity estimating unit 44 estimates at least either of scattered ray intensities (scattered X-ray intensities) at the predetermined pixels specified by the pixel specifying unit 41, and direct ray intensities (direct X-ray intensities) at the predetermined pixels. In Embodiment 1, based on the direct ray transmittances Cp calculated by the transmittance calculating unit 42, or the direct ray transmittances Cp interpolated by the transmittance interpolating unit 43, and actual measurement intensities (indicated "G" in FIG. 4) which are intensities after transmission through the grid 6 in an actual measurement taken in the presence of a subject M, the intensity estimating unit 44 estimates transmission scattered ray intensities (indicated "Sc" in FIG. 4) and estimated direct ray intensities (indicated "P" in FIG. 4), and feeds the intensities to the rate of change calculating unit 46 and display 5. In Embodiment 1, the intensity estimating unit 44 estimates the transmission scattered ray intensities Sc and estimated direct ray intensities P by solving the simultaneous equations, and therefore data "denominator" relating to the denominator included in the solution is also obtained. The intensity estimating unit 44 feeds the data "denominator" to the pixel specifying unit 41.

Using the intensities estimated by the intensity estimating unit 44 based on the actual measurement in the presence of a subject M, the rate of change calculating unit 46 calculates a value of each pixel from an average value or smoothing and interpolation calculations, as reference intensity about all the pixels relating to the intensities, and calculates a rate of change of each pixel relative to the calculated value. This is reflected in the X-raying of different subjects M, using the rates of change estimated by the intensity estimating unit 44, or the rates of change interpolated by the rate of change interpolating unit 47. In Embodiment 1, rates of change (indicated "Rcs" in FIG. 4) are calculated using the transmission scattered ray intensities Sc estimated by the intensity estimating unit 44, and are fed to the intensity estimating unit 44 again. The rates of change Rcs obtained in this way are fed to the rate of change map generating unit 48. A rate of change map M1 generated there is fed to the smoothing unit 49.

In Embodiment 1, an actual X-raying follows a procedure as shown in FIG. 5.

(Step S1) Actual Measurement Without Subject

X-raying is carried out in the absence of a subject. As shown in FIG. 6, X-rays are emitted from the X-ray tube 2 toward the grid 6 and FPD 3 with no subject interposed between the X-ray tube 2 and grid 6, thereby to carry out X-raying for actual measurement without a subject. That is, the X-ray tube 2 emits X-rays in the absence of a subject, to be incident on the FPD 3 through the grid 6, thereby obtaining actual measurement data without a subject. Specifically, the detecting elements d of the FPD 3 (see FIG. 3) read the X-rays as converted to electric signals without a subject, and provide pixel values corresponding to the electric signals.

(Step S2) Calculation and Interpolation of Direct Ray Transmittances

The pixel values are equivalent to the intensities after transmission through the grid 6 which are obtained by actual measurement without a subject. On the other hand, the intensity before transmission through the grid 6 is known. The direct ray transmittances Cp, which are between direct rays before transmission through the grid 6 (pre-transmission) and those after transmission through the grid 6 (post-transmission), are expressed by ratios between the intensity before transmission through the grid 6 and the intensities after transmission through the grid 6 (that is, the pixel values detected by the FPD 3).

Thus, the intensities after transmission through the grid 6 which are equivalent to the pixel values obtained from the FPD and the known intensity before transmission through the grid 6 are fed to the transmittance calculating unit 42. The transmittance calculating unit 42 calculates the direct ray transmittances Cp expressed by the ratios between the intensity before transmission and the intensities after transmission through the grid 6. The transmittance calculating unit 42 calculates such direct ray transmittances Cp with respect to the discrete distances between the X-ray tube 2 and the grid 6/FPD 3. Since the grid 6 and FPD 3 are arranged close to each other, the distance between the X-ray tube 2, grid 6 and FPD 3 is a distance (SID: Source Image Distance) from the focus of the X-ray tube 2 to the detecting plane (incidence plane) of the FPD 3.

The distance SID from the focus of the X-ray tube 2 to the detecting plane of the FPD 3 varies in actual X-raying as shown in FIG. 6. Then, X-raying is carried out similarly without a subject, and the transmittance calculating unit 42 obtains a direct ray transmittance Cp for each of discrete distances $L_{s+1}, L_{s+2}, L_{s+3}$ and so on as shown in black dots in FIG. 7. The direct ray transmittances Cp for the discrete distances $L_{s+1}, L_{s+2}, L_{s+3}$ and so on are fed to the transmittance interpolating unit 43 and intensity estimating unit 44. The transmittance calculating unit 42 obtains a direct ray transmittance Cp for each pixel also, and feeds it to the transmittance interpolating unit 43 and intensity estimating unit 44.

The transmittance interpolating unit 43 interpolates the direct ray transmittances Cp calculated by the transmittance calculating unit 42 in distances around the discrete distances $L_{s+1}, L_{s+2}, L_{s+3}$ and so on. The results of the interpolation are, for example, as shown in the solid line in FIG. 7. As a method of interpolation, a value acquired from an arithmetic average (additive average) or geometric average of two direct ray transmittances Cp with respect to adjoining discrete distances (e.g. $L_{s+1}$ and $L_{s+2}$) may be used as direct ray transmittance Cp for the distance between the above adjoining discrete distances. Lagrange interpolation may be used. Or the least square method may be used to obtain, as direct ray transmittance Cp, a value corresponding to a distance on the solid line, using an approximate expression of the solid line in FIG. 7. Thus, any commonly used method of interpolation may be employed. The direct ray transmittances Cp interpolated by the transmittance interpolating unit 43 are fed to the intensity estimating unit 44.

(Step S3) Actual Measurement with Phantom

Next, X-raying is carried out in the presence of a subject M. As shown in FIG. 8, acting as the subject M is a phantom Ph in the form of a flat acrylic plate regarded as providing a fixed thickness for direct ray transmission, or the same value of estimated direct ray intensity P for all the pixels.

Returning to the description of Embodiment 1, X-rays are emitted from the X-ray tube 2 toward the grid 6 and FPD 3 with the acrylic plate phantom Ph interposed between the X-ray tube 2 and grid 6, thereby to carry out X-raying for actual measurement in the presence of the phantom Ph. That is, the X-ray tube 2 emits X-rays in the presence of the subject, to be incident on the FPD 3 through the grid 6, thereby obtaining actual measurement intensities G with the phantom Ph, which intensities G are intensities after transmission through the grid 6 in actual measurement. Specifically, the detecting elements d of the FPD 3 (see FIG. 3) read the X-rays as converted to electric signals in the presence of phantom Ph, and provide pixel values corresponding to the electric signals.

(Step S4) Estimation of Intensities

The pixel values are equivalent to the actual measurement intensities G after transmission through the grid 6 which are obtained by actual measurement with the phantom Ph. On the other hand, the pixel specifying unit 41 specifies the three adjoining pixels (n−1), n and (n+1) as a combination of three pixels as noted hereinbefore. Based on the direct ray transmittances Cp calculated by the transmittance calculating unit 42, the direct ray transmittances Cp interpolated by the transmittance interpolating unit 43, and the actual measurement intensities G equivalent to the pixel values from the FPD 3, the intensity estimating unit 44 estimates transmission scattered ray intensities Sc and estimated direct ray intensities P at the three adjoining pixels (n−1), n and (n+1) specified by the pixel specifying unit 41.

The actual measurement intensities G are obtained from the actual measurement in step S3, and are known. The direct ray transmittances Cp are obtained from the actual measurement in step S1 and calculated and interpolated in step S2, and are known. On the other hand, the transmission scattered ray intensities Sc and estimated direct ray intensities P are values to be estimated by the intensity estimating unit 44, and are unknown at this point of time. Then, the intensity estimating unit 44 estimates transmission scattered ray intensity Sc and estimated direct ray intensity P by solving simultaneous equations for each of the three adjoining pixels (n−1), n and (n+1).

For the three adjoining pixels (n−1), n and (n+1), the actual measurement intensities G are set to $G_{n-1}$, $G_n$ and $G_{n+1}$, the direct ray transmittances Cp to $Cp_{n-1}$, $Cp_n$ and $Cp_{n+1}$, the transmission scattered ray intensities Sc to $Sc_{n-1}$, $Sc_n$ and $Sc_{n+1}$, and the estimated direct ray intensities P to $P_{n-1}$, $P_n$ and $P_{n+1}$. The transmission scattered ray intensity Sc varies among the three adjoining pixels due to nonuniformity of the grid 6 (scattered radiation removing device), for example. Taking this into consideration, transmission scattered ray intensities Sc at the adjoining pixels are obtained by interpolating calculation. In Embodiment 1, it is assumed that variations in the transmission scattered ray intensity Sc within the three adjoining pixels (n−1), n and (n+1) can be collinearly approximated as in the following the equation (1):

$$Sc_n = (Sc_{n+1} + Sc_{n-1})/2 \quad (1)$$

As a method of interpolating the transmission scattered ray intensities Sc, Lagrange interpolation, for example, may be used as noted in connection with the interpolation of the direct ray transmittances Cp. The method is not limited to equation (1) above, but any commonly used method of interpolation may be employed.

The actual measurement intensities G are expressed by the following simultaneous equations (2)-(4) for the three adjoining pixels (n−1), n and (n+1), showing that each actual measurement intensity G is equal to a sum of the product of estimated direct ray intensity P and direct ray transmittance Cp, and transmission scattered ray intensity Sc:

$$G_{n+1} = P_{n+1} \cdot Cp_{n+1} + Sc_{n+1} \quad (2)$$

$$G_n = P_n \cdot Cp_n + Sc_n \quad (3)$$

$$G_{n-1} = P_{n-1} \cdot Cp_{n-1} + Sc_{n-1} \quad (4)$$

Since the acrylic plate used as phantom Ph is formed to have a fixed thickness for direct ray transmission as noted hereinbefore, the estimated direct ray intensities P are equal among the three adjoining pixels as expressed by the following equation (5):

$$P_{n-1} = P_n = P_{n+1} \quad (5)$$

Thus, the pixel specifying unit 41 determines the number of certain pixels to be specified, according to the known number of known direct ray transmittances Cp and the known number of known actual measurement intensities G when estimating the unknown transmission scattered ray intensities Sc and direct ray intensities P at the three adjoining pixels (n−1), n and (n+1) specified by the pixel specifying unit 41.

The intensity estimating unit 44 will estimate the transmission scattered ray intensities Sc and direct ray intensities P by solving the simultaneous equations relating to the actual measurement intensities G, direct ray transmittances Cp, transmission scattered ray intensities Sc and estimated direct ray intensities P for the certain pixels determined, respectively.

In the above equation (1), the transmission scattered ray intensity Sc at each pixel is obtained by interpolating calculation of transmission scattered ray intensities Sc at the adjoining pixels, and therefore the number of unknowns can be reduced by one. On the other hand, since the above equation (5) shows that the estimated direct ray intensities P are equal among the three adjoining pixels, the number of unknowns is reduced to one. Therefore, apart from the above equations (1) and (5), it is sufficient to form simultaneous equations corresponding to the number of pixels specified. In this case, the simultaneous equations can be solved once the pixel specifying unit 41 specifies only an arbitrary number. In Embodiment 1, the number is set to three, and simultaneous equations are formed as the above equations (2)-(4).

By solving simultaneous equations obtained from such equations (1)-(5) noted above, the estimated direct ray intensity $P_n (= P_{n+1} = P_{n-1})$, transmission scattered ray intensities $Sc_{n-1}$, $Sc_n$ and $Sc_{n+1}$ are calculated as in the following equations (6)-(9):

$$P_n = (G_{n+1} + G_{n-1} - 2G_n) / (Cp_{n+1} + Cp_{n-1} - 2Cp_n) \quad (6)$$

$$Sc_{n+1} = G_{n+1} - P_{n+1} \cdot Cp_{n+1} \quad (7)$$

$$Sc_n = G_n - P_n \cdot Cp_n \quad (8)$$

$$Sc_{n-1} = G_{n-1} - P_{n-1} \cdot Cp_{n-1} \quad (9)$$

The estimated direct ray intensity P is first derived from the above equation (6) using the known actual measurement intensities $G_{n-1}$, $G_n$ and $G_{n+1}$ and known direct ray transmittances $Cp_{n-1}$, $Cp_n$ and $Cp_{n+1}$. After making the estimated direct ray intensity P known, transmission scattered ray intensities $Sc_{n-1}$, $Sc_n$ and $Sc_{n+1}$ are derived from the above equations (7)-(9) using also the estimated direct ray intensity $P_n (= P_{n+1} = P_{n-1})$ now known.

When the combination of three adjoining pixels (n−1), n, and (n+1) is made one group in this way, one estimated direct ray intensity $P_n$ can be found for each group. As described in relation with the above equation (5), the estimated direct ray intensities $P_n$ should essentially have the same value for all the groups, each consisting of three pixels. In practice, however, variations occur under the influence of transmittance variations of scattered rays in peripheral portions of the grid 6, or due to statistical fluctuation errors. In order to reduce the influence of such installation state of the grid 6 or statistical fluctuation errors, an average value of estimated direct ray intensities $P_n$ is obtained from central portions with little experimental errors. When, for example, minor variations occur in the above peripheral portions of the grid 6, the estimated direct ray intensities $P_n$ are obtained, using the above equation (6), for a plurality of groups in central portions of the grid 6, each group consisting of a combination of three pixels (n−1), n and (n+1), and an average value P^ thereof is obtained. The average value P^ is substituted into each of the above equations (2)-(4) (that is, substituted into the following equations (10)-(12) transformed from the above equations (7)-(9)), and the transmission scattered ray inten sities $Sc_{n-1}$, $Sc_n$ and $Sc_{n+1}$ are calculated again for all the groups.

$$Sc_{n+1} = G_{n+1} - P\hat{\,} \cdot Cp_{n+1} \qquad (10)$$

$$Sc_n = G_{n+1} - P\hat{\,} \cdot Cp_n \qquad (11)$$

$$Sc_{n-1} = G_{n-1} - P\hat{\,} \cdot Cp_{n-1} \qquad (12)$$

Thus, the intensity estimating unit 44 makes estimations by deriving the transmission scattered ray intensities $Sc_{n-1}$, $Sc_n$ and $Sc_{n+1}$ from the above equations (10)-(12). The transmission scattered ray intensities $Sc_{n-1}$, $Sc_n$ and $Sc_{n+1}$ estimated by the intensity estimating unit 44 are fed to the rate of change calculating unit 46 and display 5.

Directing attention to the denominator included in the solution of the above simultaneous equations (1)-(5), it is "$Cp_{n+1}+Cp_{n-1}-2Cp_n$" in Embodiment 1 as seen from the above equation (6). The denominator is "$Cp_{n+1}+Cp_{n-1}-2Cp_n$" even when the above equation (6) is substituted into the above equations (7)-(9). When the absolute value of the denominator "$Cp_{n+1}+Cp_{n-1}-2Cp_n$" is a certain value or less, there is a possibility that these simultaneous equations cannot be solved.

Particularly when the denominator "$Cp_{n+1}+Cp_{n-1}-2Cp_n$" is "0", the above simultaneous equations (1)-(5) cannot be solved. When the denominator "$Cp_{n+1}+Cp_{n-1}-2Cp_n$" is "0", that is when the direct ray transmittance $Cp_n$ at the middle pixel of the adjoining pixels is an arithmetical average of direct ray transmittances $Cp_{n+1}$ and $Cp_{n-1}$ of the other pixels ($Cp_{n+1}+Cp_{n-1}-2Cp_n=0$, i.e. $Cp_n=(Cp_{n+1}+Cp_{n-1})/2$), the simultaneous equations cannot be solved if the pixel specifying unit 41 selects the three pixels (n−1), n, and (n+1) as the combination for the simultaneous equations at that time. When the denominator "$Cp_{n+1}+Cp_{n-1}-2Cp_n$" is "0", the pixel specifying unit 41, preferably, does not select the three pixels (n−1), n and (n+1) as the combination for the simultaneous equations, but selects three different pixels (n'−1), n' and (n'+1) (e.g. pixels n, (n+1) and (n+2), or pixels (n−2), (n−1) and n) as the combination. Then, the above simultaneous equations (1)-(5) of the three different pixels (n'−1), n' and (n'1) specified are solved.

With the pixels specified as described above, the simultaneous equations can be solved, and using the estimated direct ray intensities $P_n$, an average value of the estimated direct ray intensities $P_n$ is obtained by the above method. Once average value $P\hat{\,}$ of the estimated direct ray intensities Pn is obtained, transmission scattered ray intensities $Sc_{n-1}$, $Sc_n$ and $Sc_{n+1}$ of the three pixels (n−1), n and (n+1) forming the combination when the denominator "$Cp_{n+1}+Cp_{n-1}-2Cp_n$" is "0" can also be derived from the above equations (10)-(12).

To summarize the description about solving the simultaneous equations, the estimated direct ray intensities $P_n$ (=$P_{n+1}$=$P_{n-1}$) when the denominator "$Cp_{n+1}+Cp_{n-1}-2Cp_n$" is not "0" are derived from the above equation (6), and average value $P\hat{\,}$ is obtained. The average value $P\hat{\,}$ is substituted into the above equations (10)-(12) to obtain the transmission scattered ray intensities $Sc_{n-1}$, $Sc_n$ and $Sc_{n+1}$ when the denominator "$Cp_{n+1}+Cp_{n-1}-2Cp_n$" is not "0". The transmission scattered ray intensities $Sc_{n-1}$, $Sc_n$ and $Sc_{n+1}$ when the denominator "$Cp_{n+1}+Cp_{n-1}-2Cp_n$" is "0" can also be obtained by similar substitution into the above equations (10)-(12). In this way, the estimated direct ray intensities P when the denominator "$Cp_{n+1}+Cp_{n-1}-2Cp_n$" is not "0" are first obtained to obtain average value $P\hat{\,}$. Then, the average value $P\hat{\,}$ is used to obtain the transmission scattered ray intensities $Sc_{n-1}$, $Sc_n$ and $Sc_{n+1}$ when the denominator "$Cp_{n+1}+Cp_{n-1}-2Cp_n$" is not "0", and the transmission scattered ray intensities $Sc_{n-1}$, $Sc_n$ and $Sc_{n+1}$ when the denominator "$Cp_{n+1}+Cp_{n-1}-2Cp_n$" is "0" are obtained similarly.

In this method, the subject is the phantom Ph in the form of an acrylic plate, and variations in the estimated direct ray intensity P are known and smooth. These facts are used to obtain the estimated direct ray intensity P (average value $P\hat{\,}$ in Embodiment 1) by smoothing and interpolating calculations of the estimated direct ray intensities P obtained about the pixels (specified pixels) first determined by the pixel specifying unit 41, or by calculating an average value of the estimated direct ray intensities P. The estimated direct ray intensity P obtained has a value close to a true value since variations of the estimated direct ray intensity P are smooth, and averaging or smoothing is effective in reducing variations due to statistical fluctuation errors. The transmission scattered ray intensities Sc are obtained directly by substituting the estimated direct ray intensity P close to the true value into the above equations (2)-(4). This provides a great advantage of causing no deterioration in the resolution of images of the transmission scattered ray intensities Sc since averaging or smoothing and interpolating calculations are not carried out. The resolution of the transmission scattered ray intensities Sc is maintained, and minute variations in the transmission scattered ray intensity Sc due to deformation of the grid foil strips can be determined accurately.

As another method, for example, transmission scattered ray intensities $Sc_{n-1}$, $Sc_n$ and $Sc_{n+1}$ when the denominator "$Cp_{n+1}+Cp_{n-1}-2Cp_n$" is not "0" may be obtained before the estimated direct ray intensities P. By interpolating the transmission scattered ray intensities $Sc_{n-1}$, $Sc_n$ and $Sc_{n+1}$, transmission scattered ray intensities $Sc_{n-1}$, $Sc_n$ and $Sc_{n+1}$ when the denominator "$Cp_{n+1}+Cp_{n-1}-2Cp_n$" is "0" are obtained. By substituting the obtained transmission scattered ray intensities $Sc_{n-1}$, $Sc_n$ and $Sc_{n+1}$ into the above equations (7)-(9), estimated direct ray intensities P when the denominator "$Cp_{n+1}+Cp_{n-1}-2Cp_n$" is not "0" and when the denominator "$Cp_{n+1}+Cp_{n-1}-2Cp_n$" is "0" are obtained. An average value $P\hat{\,}$ of a plurality of estimated direct ray intensities $P_n$ of the combination of three pixels (n−1), n and (n+1) in the central portion of the grid 6, including when the denominator "$Cp_{n+1}+Cp_{n-1}-2Cp_n$" is "0", is obtained. By substituting this average value $P\hat{\,}$ into the above equations (10)-(12), transmission scattered ray intensities $Sc_{n-1}$, $Sc_n$ and $Sc_{n+1}$ may be obtained again. The transmission scattered ray intensities $Sc_{n-1}$, $Sc_n$ and $Sc_{n+1}$ obtained again may be used to obtain rates of change Rcs in step S5 described hereinafter.

(Step S5) Calculation and Interpolation of Rates of Change

The rate of change calculating unit 46 calculates rates of change Rcs using the transmission scattered ray intensities Sc ($Sc_{n-1}$, $Sc_n$ and $Sc_{n+1}$) estimated by the intensity estimating unit 44. Specifically, an average value $Sc\hat{\,}$ is obtained, or values Sc~ of pixels are obtained by smoothing and interpolating calculations, in order to determine the rates of change Rcs of the pixels relative to the values of all the pixels as reference intensities of the transmission scattered ray intensities Sc. Assuming that a ratio between the transmission scattered ray intensity $Sc_n$ of each pixel and the average value $Sc\hat{\,}$ or the value Sc~ of each pixel is a rate of change Rcs, and that $Rcs_n$ represents the rate of change Rcs of each pixel, $Rcs_n$ is expressed by the following equation (13):

$$Rcs_n = Sc_n/Sc\hat{\,}$$

$$\text{or } Rcs_n = Sc_n/Sc\sim \qquad (13)$$

A reference estimated scattering intensity used as the denominator when calculating the rates of change of transmission scattered rays corresponds to scattered ray intensity in the case of an ideal grid with no distortion of the foil strips or not dependent on installation conditions.

As a method therefor may use:

1) an average value by simply approximating a scattered ray intensity distribution two-dimensionally fixed; or 2) a value acquired by two-dimensionally smoothing and interpolating the estimated scattered ray intensity of each pixel, by strictly taking into consideration scattered ray intensity variations due to installation conditions, such as the shape of the phantom and peripheral portions of the grid. The average value of 1) can be said the simplest method of smoothing and interpolating calculations.

Thus, variations of transmission scattered ray intensity Sc, for which installation conditions of the grid 6 relating to deformation of the absorbing foil strips 6a, for example, are considered by using the ratio relative to the reference value, are expressed by the rates of change $Rcs_n$. The rate of change calculating unit 46 calculates the rates of change $Rcs_n$ for all the pixels. The rate of change interpolating unit 47 interpolates, as necessary, the rates of change $Rcs_{n-1}$, $Rcs_n$ and $Rcs_{n+1}$ calculated by the rate of change calculating unit 46, and then feeds the rates of change to the intensity estimating unit 44 again.

The rate of change Rcs, as does the direct ray transmittance Cp, varies for each of the discrete distances $L_{s+1}$, $L_{s+2}$ and $L_{s+3}$ as shown in black squares in FIG. 7. The rate of change interpolating unit 47 interpolates the rates of change Rcs calculated by the rate of change calculating unit 46 in distances around the discrete distances $L_{s+1}$, $L_{s+2}$, $L_{s+3}$ and so on. The results of the interpolation are, for example, as shown in the dotted line in FIG. 7. As a method of interpolation, a value acquired from an arithmetic average (additive average) or geometric average of two rates of change Rcs with respect to adjoining discrete distances (e.g. $L_{s+1}$ and $L_{s+2}$) may be used as rate of change Rcs for the distance between the above adjoining discrete distances. Lagrange interpolation may be used. Or the least square method may be used to obtain, as rate of change Cp, a value corresponding to a distance on the dotted line, using an approximate expression of the dotted line in FIG. 7. Thus, any commonly used method of interpolation may be employed.

(Step S6) Generation of Average Value Map

The rates of change Rcs obtained as described above correspond to the detecting elements d of the FPD 3, respectively. Thus, by mapping the rates of change Rcs with reference to the detecting elements d, the rate of change map M1 is generated which shows a striped pattern of scattered rays reflected in the FPD 3. This rate of change map M1 is generated by the rate of change map generating unit 48. The rate of change map M1 generated is stored in a rate of change map storage unit 48a.

Characteristics of this rate of change map M1 will be described. The absorbing foil strips 6a of the grid 6 extend along one direction in the arrangement of the detecting elements d of FPD 3. The rates of change Rcs are alike when compared along this direction. However, the rates of change Rcs differ from one another when compared along the direction of arrangement of the absorbing foil strips 6a. FIG. 9 schematically represents such a situation.

The rates of change Rcs constituting the rate of change map M1 will be described further. The rates of change Rcs include components of a pattern appearing on a fluoroscopic image due to differences in transmission condition of scattered rays for varied parts of the FPD 3. It is ideal if the rates of change Rcs include only components of the pattern, but in practice this is not the case. That is, the rates of change Rcs include also variations (statistical noise) due to the intensity of direct rays incident on the detecting elements d.

Figure 10:
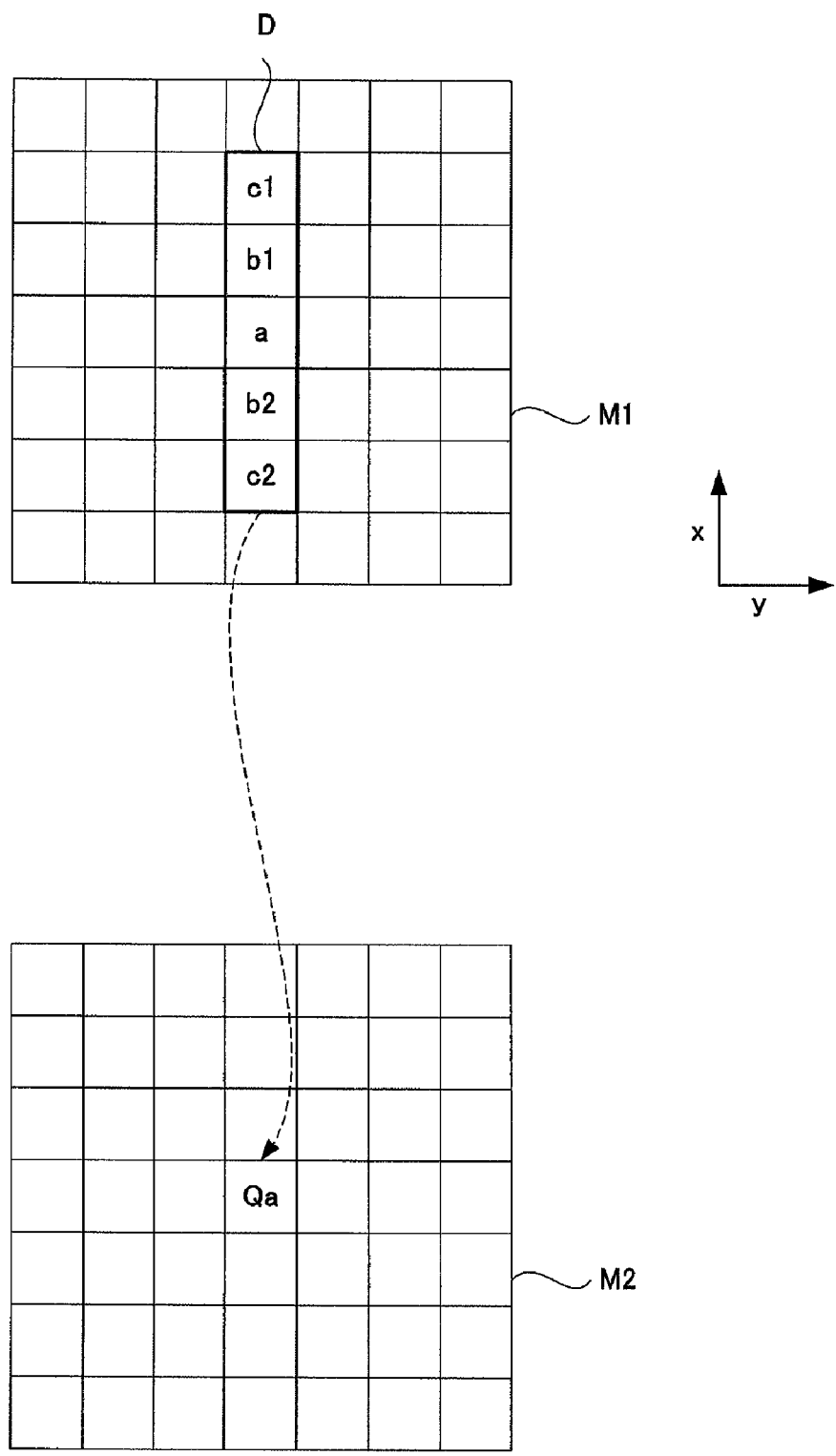
FIG. 10 is a schematic view illustrating smoothing according to Embodiment 1.

The rate of change map M1 is outputted to the smoothing unit 49. There, the rate of change map M1 is smoothed to remove the influence of the above statistical noise from the rate of change map M1. This smoothing of the rates of change differs in character from the smoothing process in step S5 described hereinbefore. Specifically, the rate of change map M1 is smoothed using the rates of change located in a line in the direction along the X-ray grid. FIG. 10 shows a rate of change "a" belonging to the rate of change map M1 as the target of smoothing. First, a domain D is set to include rates of change located in a line with the rate of change "a" in the middle. Then, an average value Qa is obtained of the rates of change a, b1, b2, c1 and c2 belonging to the domain D. This operation is carried out for all the rates of change belonging to the rate of change map M1. That is, average value Qcs corresponding to each of the rates of change will be acquired. By arranging the average values Qcs with reference to positions of the rates of change in the rate of change map M1, an average value map M2 which is a new map will be acquired. Although the domain D includes five rates of change, the number can be varied freely. The average value map M2 is stored in an average value map storage unit 49a.

The rate of change serving as the target of smoothing need not necessarily be located in the middle of domain D. That is, it is conceivable that the rates of change b1, b2, c1 and c2 in FIG. 10 do not exist for a rate of change located peripherally of the rate of change map M1. In that case, smoothing can be carried out without setting the rate of change as the target of smoothing to the middle of domain D.

The effect of such smoothing will be described. FIGS. 11A and 11B are schematic views illustrating the effect of smoothing according to the construction in Embodiment 1. FIG. 11A shows the rates of change a, b1, b2, c1 and c2 belonging to the domain D which is the construction in Embodiment 1. That is, each rate of change has a component K1 due to the statistical noise, and a component K2 due to the striped pattern of scattered rays. The component K2 due to the striped pattern of scattered rays in each rate of change extending along the direction of extension (X-direction) of the absorbing foil strips of the X-ray grid is similar to those of the other rates of change belonging to domain D. Thus, the component K2 is maintained in the average value Qa. On the other hand, the component K1 is varied among the rates of change belonging to the domain D, and is therefore averaged.

For comparison, results of a similar operation carried out for rates of change a, b3, b4, c3 and c4 located in a line extending in the direction perpendicular to the absorbing foil strips are shown. This situation is shown in FIG. 11B. It will be seen that the component K2 due to the striped pattern of scattered rays is not uniform among the rates of change a, b3, b4, c3 and c4, and that, upon comparison, the component K2 of the average value is different from that of the rate of change "a". When the average value is calculated for the rates of change a, b3, b4, c3 and c4, the value of component K2 included in the average value A will differ from what is included in the rate of change "a". Since the striped pattern of scattered rays is included in the components K2, the values of K2 changed by the smoothing will blur the striped pattern of scattered rays on the average value map M2. Such construction is not employed in Embodiment 1.

(Step S7) Actual Measurement with Real Subject

Next, X-raying is carried out in the presence of a subject M other than the subject M (phantom Ph) used in steps S3-S6. As shown in FIG. 1, a real subject M is used for actual X-raying. X-rays are emitted from the X-ray tube 2 toward the grid 6 and FPD 3 with the real subject M interposed between the X-ray tube 2 and grid 6, thereby to carry out X-raying for actual measurement with the real subject M. That is, the X-ray tube 2 emits X-rays in the presence of the real subject M (i.e. subject M for use in actual X-raying), to be incident on the FPD 3 through the grid 6. In this way, actual measurement intensities G which are intensities after transmission through the grid 6 in the actual measurement in the presence of the subject M are obtained as in step S3. Specifically, the detecting elements d of the FPD 3 (see FIG. 3) read the X-rays as converted to electric signals in the presence of the subject M, and provide pixel values corresponding to the electric signals.

(Step S8) Estimation and Interpolation of Intensities

As noted in step S4, the pixel values are equivalent to the actual measurement intensities G after transmission through the grid 6 which are obtained by actual measurement with the subject M. Similarly, the pixel specifying unit 41 specifies the three adjoining pixels (n−1), n and (n+1) as a combination of three pixels. Based on the average values Qcs stored in the average value map storage unit 49a, the direct ray transmittances Cp calculated by the transmittance calculating unit 42 or the direct ray transmittances Cp interpolated by the transmittance interpolating unit 43, and the actual measurement intensities G equivalent to the pixel values from the FPD 3, the intensity estimating unit 44 again estimates transmission scattered ray intensities Sc and estimated direct ray intensities P at the three adjoining pixels (n−1), n and (n+1) specified by the pixel specifying unit 41.

As in step S4, the transmission scattered ray intensities Sc and estimated direct ray intensities P are estimated by solving simultaneous equations. Differences to step S4 lie in that a parameter consisting of the average values Qcs is taken into consideration, and that the equations concerning the transmission scattered ray intensities Sc and estimated direct ray intensities P are different. The aspects common to step S4 will not be described.

In step S8, the transmission scattered ray intensities Sc are transmission scattered ray intensities where there is no foil nonuniformity such as deformation of the absorbing foil strips of the grid 6 and the installation condition is ideal. The transmission scattered ray intensities Sc vary smoothly where, apart from the rates of change due to nonuniformity of the grid 6, the subject is a water column (e.g. a water pillar) or a human body and the radiation is X-rays or gamma rays. Thus, the transmission scattered ray intensities Sc are considered equal among the three adjoining pixels, as expressed by the following equation (1)".

$$Sc_{n-1}=Sc_n=Sc_{n+1} \quad (1)''$$

The actual measurement intensities G are expressed by the following simultaneous equations (2)"-(4)" for the three adjoining pixels (n−1), n and (n+1), showing that each actual measurement intensity G is equal to a sum of the product of estimated direct ray intensity P and direct ray transmittance Cp, and the product of transmission scattered ray intensity Sc and average value Qsc:

$$G_{n+1}=P_{n+1} \cdot Cp_{n+1}+Sc_{n+1} \cdot Qcs_{n+1} \quad (2)''$$

$$G_n=P_n \cdot Cp_n+Sc_n \cdot Qcs_n \quad (3)''$$

$$G_{n-1}=P_{n-1} \cdot Cp_{n-1}+Sc_{n-1} \cdot Qcs_{n-1} \quad (4)''$$

As distinct from the case of the phantom Ph in the form of an acrylic plate in step S3, the estimated direct ray intensity P at each pixel is variable due to the shape and material of the subject M. The variations can be expressed by interpolating calculations of the estimated direct ray intensities P at adjoining pixels. In Embodiment 1, it is assumed that the variations in the estimated direct ray intensities P within the three adjoining pixels (n−1), n and (n+1) can be collinearly approximated as in the following the equation (5)":

$$P_n=(P_{n+1}+P_{n-1})/2 \quad (5)''$$

As a method of interpolating the estimated direct ray intensities P, Lagrange interpolation, for example, may be used as noted in connection with the interpolation of the direct ray transmittances Cp and the interpolation of transmission scattered ray intensities Sc in step S4. The method is not limited to equation (5)" above, but any commonly used method of interpolation may be employed.

By solving simultaneous equations obtained from such equations (1)"-(5)" noted above, the estimated direct ray intensities $P_{n-1}$, $P_n$ and $P_{n+1}$, transmission scattered ray intensity $Sc_n$ ($=Sc_{n+1}=Sc_{n-1}$) are calculated as in the following equations (6)"-(9)":

$$Sc_n=G_{n+1}/Qcs_{n+1}-\{(Cp_n \cdot Qcs_{n-1}-2Cp_{n-1} \cdot Qcs_n) \cdot G_{n+1}+ \\ 2Cp_{n-1} \cdot Qcs_{n+1} \cdot G_n-Cp_n \cdot Qcs_{n+1} \cdot G_{n-1}\}/ \\ (Cp_{n+1} \cdot Cp_n \cdot Qcs_{n+1} \cdot Qcs_{n-1}-2Cp_{n+1} \cdot Cp_{n-1} \cdot \\ Qcs_{n+1} \cdot Qcs_n+Cp_n \cdot Cp_{n-1} \cdot Qcs_{n+1}^2) \quad (6)''$$

$$P_{n-1}=\{(Cp_n \cdot Qcs_{n-1}-2Cp_{n-1} \cdot Qcs_n) \cdot G_{n+1}+ \\ 2Cp_{n-1} \cdot Qcs_{n+1} \cdot G_n-Cp_n \cdot Qcs_{n+1} \cdot G_{n-1}\}/ \\ (Cp_{n-1} \cdot Cp_n \cdot Qcs_{n-1}-2Cp_{n+1} \cdot Cp_{n-1} \cdot Qcs_n+ \\ Cp_n \cdot Cp_{n-1} \cdot Qcs_{n+1}) \quad (7)''$$

$$P_n=G_n/Cp_n-Qcs_n \cdot [G_{n+1}/Qcs_{n+1}\{(Cp_n \cdot Qcs_{n-1}- \\ 2Cp_{n-1} \cdot Qcs_n) \cdot G_{n+1}+2Cp_{n-1} \cdot Qcs_{n+1} \cdot G_n- \\ Cp_n \cdot Qcs_{n+1} \cdot G_{n-1})/(Cp_{n+1} \cdot Cp_n \cdot Qcs_{n+1} \cdot Qcs_{n-1}- \\ 2Cp_{n+1} \cdot Cp_{n1} \cdot Qcs_{n+1} \cdot Qcs_n+Cp_n \cdot Cp_{n-1} \cdot Qcs_{n+1}^2)] \quad (8)''$$

$$P_{n+1}=G_{n+1}/Cp_{n+1}-Qcs_{n-1} \cdot [\{(Cp_n \cdot Qcs_{n-1}- \\ 2Cp_{n-1} \cdot Qcs_n) \cdot G_{n+1}+2Cp_{n-1} \cdot Qcs_{n+1} \cdot G_n- \\ Cp_n \cdot Qcs_{n+1} \cdot G_{n-1})/(Cp_{n+1} \cdot Cp_n \cdot Qcs_{n+1} \cdot Qcs_{n-1}- \\ 2Cp_{n+1} \cdot Cp_{n-1} \cdot Qcs_{n+1} \cdot Qcs_n+Cp_n \cdot Cp_{n-1} \cdot Qcs_{n+1}^2)] \quad (9)''$$

The estimated direct ray intensities $P_{n-1}$, $P_n$ and $P_{n+1}$ and transmission scattered ray intensity $Sc_n(=Sc_{n+1}=Sc_{n-1})$ derived from the above equations (6)"-(9)" are values calculated when the denominator included in the solution of the above simultaneous equations (1)"-(5)" is not "0".

When the denominator included in the solution of the above simultaneous equations (1)"-(5)" is "0", the above simultaneous equations (1)"-(5)" cannot be solved. Thus, with the three pixels (n−1), n and (n+1) forming the combination resulting in the denominator "0", the estimated direct ray intensities $P_{n-1}$, $P_n$ and $P_{n+1}$ or the transmission scattered ray intensities $Sc_{n-1}$, $Sc_n$ and $Sc_{n+1}$ cannot be calculated, and thus cannot be estimated. The following method 1), for example, is one of the methods for estimating the estimated direct ray intensities $P_{n-1}$, $P_n$ and $P_{n+1}$ and the transmission scattered ray intensities $Sc_{n-1}$, $Sc_n$ and $Sc_{n+1}$.

The method 1) determines the transmission scattered ray intensities Sc first. Since the transmission scattered ray intensities Sc assume that there is no deformation of the absorbing foil strips of the grid 6 and the installation condition is ideal, a plurality of transmission scattered ray intensities $Sc_n$ acquired when the denominator is not "0" are first used in appropriate smoothing and interpolating calculations to obtain transmission scattered ray intensities $Sc_n$~ for all the pixels, including those pixels for which the transmission scattered ray intensities Sc are not yet obtained because the denominator is "0". As noted in connection with the above equation (1)", variations are smooth where the subject is a water column (e.g. a water pillar) or a human body and the radiation is X-rays or gamma rays. And smoothing is effective in reducing variations due to statistical fluctuation errors. Thus, the values $Sc_n$~ obtained are close to the true values of transmission scattered ray intensities $Sc_n$. The transmission scattered ray intensities $Sc_n$~ obtained in this way are substituted into the above equation (3) for all the pixels, thereby obtaining the estimated direct ray intensities $P_n$ directly. As noted above, this method provides a great advantage of causing no deterioration in the resolution of images of the estimated direct ray intensities $P_n$ since smoothing and interpolating calculations are not carried out from the values of the pixels for which the denominator is not "0".

Thus, as in step S4, and as described above, the transmission scattered ray intensities $Sc_n$ may be obtained first, or the estimated direct ray intensities $P_n$ may be obtained first.

Thus, X-ray images having reduced false images due to scattered rays and grid 6 are appropriately obtained through steps S1-S8, by using the estimated direct ray intensities $P_n$ obtained in step S8 as pixel values. Such X-ray images may be outputted on the display 5 noted hereinbefore, may be written and stored in a storage medium represented by a RAM (Random-Access Memory) to be read therefrom as necessary, or may be printed out by a printing device. When the transmission scattered ray intensities $Sc_n$ are obtained before the estimated direct ray intensities $P_n$ by the method 1) in step S7, X-ray images may be outputted to the display 5, storage medium or printing device after obtaining the estimated direct ray intensities $P_n$.

Since the direct ray transmittance Cp is calculated in step S2 for each distance SID from the focus of X-ray tube 2 to the detecting plane of FPD 3, the parameters obtained in steps S3-S8 are values appropriately acquired for the respective distances SID. Now, unless the distance between the subject M and FPD 3 change even if the distance SID changes, variations in the scattered ray distribution are small unlike the direct ray transmittance Cp, and variations of the average values $Qcs_n$ for the average value map can be disregarded almost altogether. In that case, an average value $Qcs_n$ may be obtained for a certain distance SID, and this value may be used for different distances SID, whereby steps S3-S5 can be omitted. Then, steps 6 et seq. may be executed to carry out actual measurement in the presence of the real subject M. When variations of average value $Qcs_n$ relative to variations of distance SID cannot be disregarded, an average value $Qcs_n$ may be obtained beforehand for each of the discrete distances $L_{s+1}$, $L_{s+2}$ and $L_{s+3}$, actual distances SID may be obtained by interpolating calculations thereof, which also can omit steps S3-S5. Then, steps 6 et seq. may be executed to carry out actual measurement in the presence of the real subject M. Thus, even when the distance SID varies in actual X-raying as shown in FIG. 6, use may be made of the direct ray transmittances Cp and the average value Qcs of the transmission scattered ray intensities Sc for which the varied distances SID are taken into consideration. This can be applied also to a circulatory organ radiographic apparatus, for example, where the distance between the X-ray tube 2 and the grid 6/FPD 3 is changed every now and then.

According to the X-ray apparatus in Embodiment 1, the X-ray tube 2 emits X-rays to be incident on the FPD 3 through the grid 6. Part of scattered X-rays (scattered rays) are removed by the grid 6, and the FPD 3 detects the remaining X-rays to obtain an X-ray image. At this time, the pixel specifying unit 41 specifies certain of the pixels forming the X-ray image. The intensity estimating unit 44 estimates at least one of scattered X-ray intensity (scattered ray intensity) and direct X-ray intensity (direct ray intensity) at the certain pixels specified by the pixel specifying unit 41. Therefore, at least one of scattered X-ray intensity (scattered ray intensity) and direct X-ray intensity (direct ray intensity) at the certain pixels can be estimated appropriately in a way to take the installation condition of the grid 6 into consideration.

Thus, according to the invention described in Embodiment 1, the X-ray tube 2 emits radiation to be incident on the FPD 3 through the grid 6. Part of scattered radiation is removed by the grid 6, and the FPD 3 detects the remaining radiation to obtain a radiographic image. At this time, the pixel specifying unit 41 specifies certain of the pixels forming the radiographic image. The intensity estimating unit 44 estimates at least one of scattered radiation intensity and direct radiation intensity at the certain pixels specified by the pixel specifying unit 41. Therefore, at least one of scattered radiation intensity and direct X-ray radiation at the certain pixels can be estimated appropriately in a way to take the installation condition of the grid 6 into consideration. Thus, radiation intensity is estimated by the radiation estimating unit 44 for the certain pixels, while radiation intensity is interpolated by the intensity interpolating device for the pixels not specified. Based on such radiation intensity, a radiographic image is obtained appropriately, which is free of shadows of the grid 6. The radiographic image is obtained only from the direct radiation with the scattered radiation removed completely. The radiographic image is obtained appropriately by the pixel specifying unit 41 and intensity estimating unit 44, with any grid 6. As a result, a general-purpose grid 6 can also be used, and a proper radiographic image can be obtained without being dependent on the installation condition of the grid 6. It is necessary to estimate radiation intensity for all the pixels. Radiation intensity may be estimated for only the certain specified pixels, and radiation intensity at the remaining pixels not specified may be determined by interpolation. This produces the effects of lightening arithmetic processes, and reducing the time consumed therefor.

According to the construction in Embodiment 1, the rate of change map generating unit 41 is provided for generating the rate of change map M1. This rate of change map M1 shows a pattern (striped pattern of scattered rays) to appear on a fluoroscopic image. The striped pattern of scattered rays will be removed by correcting the fluoroscopic image using this map M1. The smoothing unit 49 is provided for smoothing this rate of change map M1 to generate the average value map M2. The rate of change map M1 has, superimposed thereon, statistical noise besides the striped pattern of scattered rays. However, the rate of change map M1 is smoothed to become the average value map M2. In the average value map M2, the statistical noise is averaged and blurred. Even if the statistical noise tends to be reflected as granular coarse noise on the fluoroscopic image, its granularity is blurred on the average value map M2. Consequently, the statistical noise on the rate of change map M1 is never superimposed on the fluoroscopic image.

The smoothing is carried out for the rates of change Rcs arranged in a line along the direction of extension of the absorbing foil strips 6a of the grid 6. Desirably, the striped pattern of scattered rays is not blurred by the smoothing. The striped pattern of scattered rays extends along the direction of extension of the absorbing foil strips 6a of the grid 6 (in other words, the striped pattern of scattered rays is arranged along the direction of arrangement of the absorbing foil strips 6a of the grid 6). Since the smoothing is carried out along the direction of extension of the absorbing foil strips 6a of the grid 6, components of the statistical noise included in the rates of change Rcs are smoothed, but components of the striped pattern of scattered rays are not. Consequently, the striped pattern of scattered rays appearing on the rate of change map M1 is not blurred by the smoothing, and the pattern can be removed without appearing on the fluoroscopic image.

The X-ray tube 2 emits radiation in the presence of a different subject (i.e. the subject used in actual radiography here) to be incident on the FPD 3 through the grid 6, thereby to obtain actual measurement intensity which is radiation intensity after transmission through the grid 6 in actual measurement in the presence of the subject. Based on the average values Qcs stored in the average value map storage unit 49a, the direct ray transmittances calculated by the transmittance calculating unit 42, and the actual measurement intensity in the actual measurement in the presence of the different subject (i.e. the subject used in actual radiography), the intensity estimating unit 44 estimates radiation intensity at the certain pixels specified by the pixel specifying unit 41. Thus, direct ray transmittance is obtained based on the actual measurement data taken in the absence of a subject. Using the direct ray transmittance, rates of change Rcs are obtained by carrying out radiography in the presence of a subject (i.e. the phantom). Using the rates of change Rcs or the rates of change Rcs interpolated by the rate of change interpolating device, radiation intensity can be estimated based on the actual measurement intensity obtained from radiography carried out in the presence of the different subject (i.e. the subject used in actual radiography).

This invention is not limited to the foregoing embodiment, but may be modified as follows:

(1) The foregoing embodiment has been described taking X-rays as an example of radiation. However, the invention is applicable to radiation other than X-rays (such as gamma rays).

(2) In the foregoing embodiment, the radiographic apparatus is constructed for medical use to conduct radiography of a patient placed on the top board 1 as shown in FIG. 1. This is not limitative. For example, the apparatus may be constructed like a nondestructive testing apparatus for industrial use which conducts radiography of an object (in this case, a subject tested) conveyed on a belt, or may be constructed like an X-ray CT apparatus for medical use.

Figure 12:
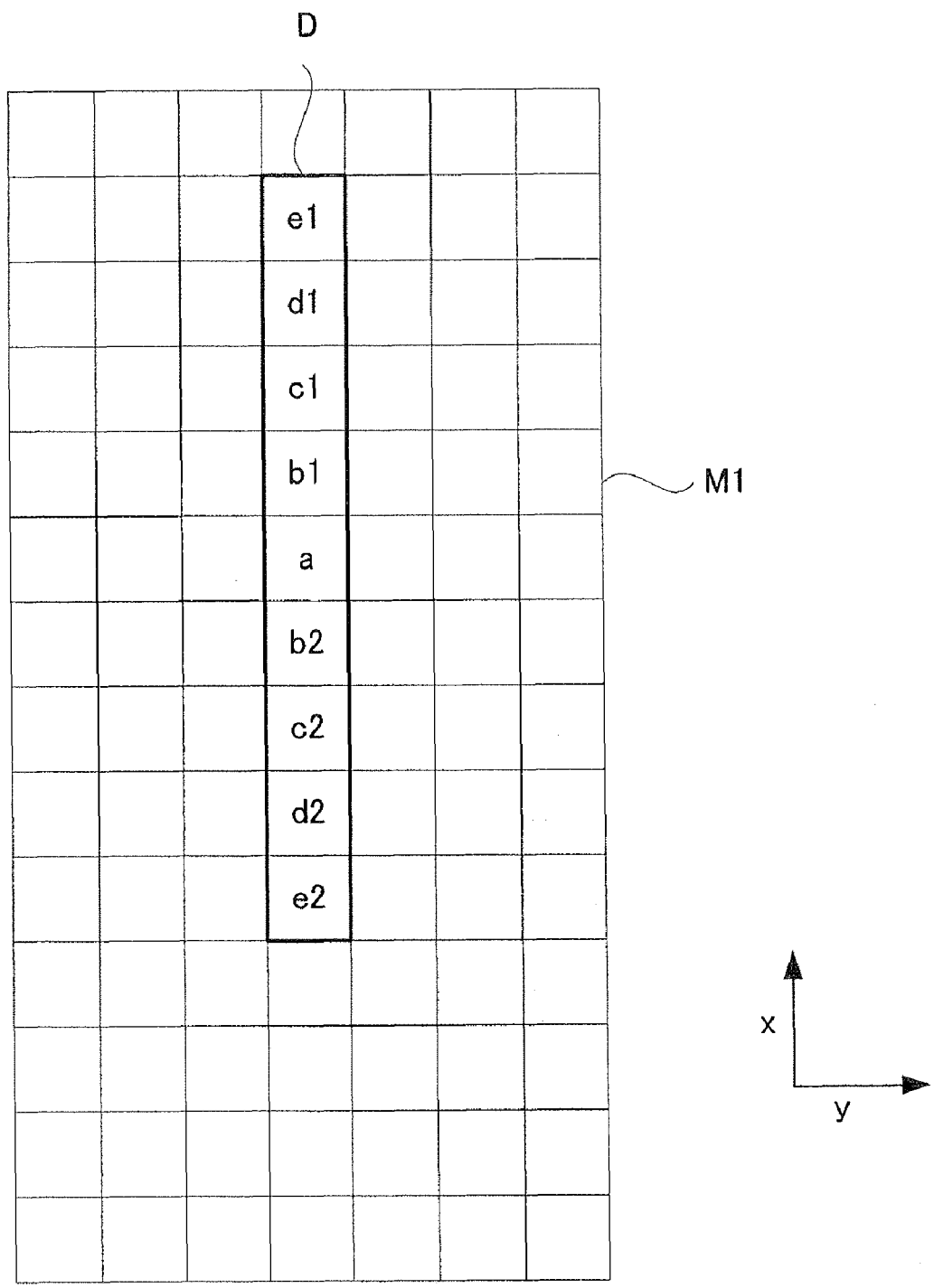
FIG. 12 is a schematic view of one modification of this invention.

(3) The rate of change map generating unit 48 described hereinbefore obtains the average value A by averaging the rates of change Rcs included in the domain D. This invention is not limited to such construction. The average value A may be obtained by weighting the rates of change belonging to the domain D according to distances to the rate of change which is the target of smoothing. That is, as shown in FIG. 12, when obtaining the average value A for the rate of change "a" which is the target of smoothing, the average value A is influenced to a greater extent by a rate of change, such as rate of change b1, closer to the rate of change "a" than a rate of change, such as rate of change e1, remote from the rate of change "a". For example, the average value A may be obtained using each of the rates of change according to the following equation:

$$A = \{1 \times (e1+e2) + 2 \times (d1+d2) + 3 \times (c1+c2) 4 \times (b1+b2) 5 \times a\}/(1+1+2+2+3+3+4+4+5) \quad (10)$$

With such construction, the striped pattern of scattered rays held by the rate of change map M1 can reliably be unblurred.

(4) In the foregoing embodiment, the method in step S5 has been described in which, using the transmission scattered ray intensities Sc estimated based on the actual measurement carried out in the presence of a subject, a rate of change for each pixel is determined with respect to an average value of all the pixels relating to the transmission scattered ray intensities Sc. However, there is another method of obtaining rates of change of transmission scattered rays, which obtains rates of change Rcs by actual measurement in the absence of a subject. As an artificial source of scattered rays (without direct rays), the radiation source is made to scan the grid two-dimensionally to cause direct rays to be incident on the scattered radiation removing device from a large range, so that the direct rays are equivalent to scattered rays. Rates of change Rcs are obtained from an integrated value thereof through determining a ratio with respect to an average value of all the pixels. Whichever method may be used.

(5) In the foregoing embodiment, the number of certain pixels to be selected by the pixel specifying device (pixel specifying unit 41 in the embodiment) is three. But the number of such pixels is not limited to three. The number may be determined according to simultaneous equations.

(6) In the foregoing embodiment, the pixel specifying device (pixel specifying unit 41 in the embodiment) does not select the certain pixels forming a combination for simultaneous equations when the absolute of the denominator included in the solution of the simultaneous equations has a predetermined value or less. The predetermined value is not limited to "0" noted hereinbefore. As the denominators included in the solutions of the simultaneous equations in the foregoing embodiment, there are the denominator included in the estimated direct ray intensity Pn in "(Step S2) Calculation and interpolation of direct ray transmittances", and the denominator included in the transmission scattered ray intensity Sc in "(Step S8) Estimation and interpolation of intensities". The relatively simple denominator ($Cp_{n+1}+Cp_{n-1}-2Cp_n$) included in the estimated direct ray intensity Pn in "(Step S2) Calculation and interpolation of direct ray transmittances" will be described.

For example, when a pixel shielded by the grid foil strips is n and non-shielded pixels are n+1 and n−1, and when there is no distortion of the foil strips, the value of direct ray transmittance Cp of each at that time can be calculated beforehand. When, for example, the width of the pixels is 150 μm, the thickness of the grid foil strips is 30 μm, and the intermediate substance is air, with absorption by the grid cover disregarded, $Cp_{n+1}=1$, $Cp_{n-1}=1$ and $Cp_n=0.7$. Therefore, the denominator at this time is $Cp_{n+1}+Cp_{n-1}-2Cp_n=1+1-2\times 0.7=0.6$.

On the other hand, the numerator of $P_n$ is ($G_{n+1}+G_{n-1}-2G_n$). Its statistical fluctuation error can be predicted from statistical fluctuation errors of $G_{n+1}$, $G_{n-1}$ and $G_n$, and the statistical fluctuation error of $P_n$ finally obtained has a value resulting from a division by the value of the denominator. This is 0.6 in an ideal installation condition of the foil strips in the above example, and its value may become small when the foil strips are distorted, for example. When the statistical fluctuation error of the numerator is divided by this value, the statistical fluctuation error will becomes large, giving a large error to the average value of $P_n$ to be calculated afterward. Therefore, when a tolerance is three times an ideal case, for example, the predetermined value of the denominator is 0.2, and only a reliable value of $P_n$ can be calculated. In this way, a predetermined value may be set to specify the pixels.

Similarly, in the case of (Step S8), a comparison is made with the value of the denominator in the normal case, and a predetermined value may be selected based on the tolerance of the statistical fluctuation error of Sn which can finally be obtained. In each of the above cases, the predetermined value is set with reference to a tolerance of the statistical fluctuation error of the value sought. The predetermined value may be set based on a different reference value.

(7) In the foregoing embodiment, the transmission scattered ray intensity and estimated direct ray intensity are estimated. However, only one of these intensities may be estimated.

(8) The term "pixel" as used in this specification includes not only each pixel not subjected to a bundling process (binning), but also a plurality of pixels bundled together (binned) to be regarded as one pixel. Therefore, when specifying pixels, or using specified pixels, such pixels may be considered binned or may be considered not binned.

(9) In the foregoing embodiment, the rate of change calculating device is provided as a component corresponding to the physical quantity acquiring device. The rate of change map generating device is provided as a component corresponding to the physical quantity map generating device. The rate of change map smoothing device is provided as a component corresponding to the physical quantity map smoothing device. The rates of change Rcs are arranged to generate the rate of change map M1, and the latter is smoothed to generate the average value map M2. However, this invention is not limited to such construction. An average value map M2 may be generated by arranging the direct ray transmittances Cp, transmission scattered ray intensities Sc or estimated direct ray intensities P instead of the rates of change Rcs. Then, the image processor 4 can carry out the image processes after removing the statistical noise superimposed on the direct ray transmittances Cp, transmission scattered ray intensities Sc or estimated direct ray intensities P. It is therefore possible to acquire images free of both the striped pattern of scattered rays and the statistical noise.

(10) The smoothing of the rates of change map M1 using the smoothing unit 49 need not always to be adapted to all the rates of change map M1, but may be optionally adapted to a part of the rates of change map M1 as necessary.

(11) In the foregoing embodiment, the grid 6 has the absorbing foil strips 6a arranged in the single direction, which may be replaced with a cross grid. The cross grid has a lattice structure with elongated absorbing foil strips arranged in a crisscross pattern. In this case, the smoothing unit 49 selects one of the longitudinal and transverse directions (X-direction and Y-direction) of the rate of change map M1, and obtains average values of the rates of change Rcs arranged in a line in the selected direction. The average value map M2 may be generated by combining calculations of average values in the longitudinal direction, and calculations of average values in the transverse direction.

Figure 13:
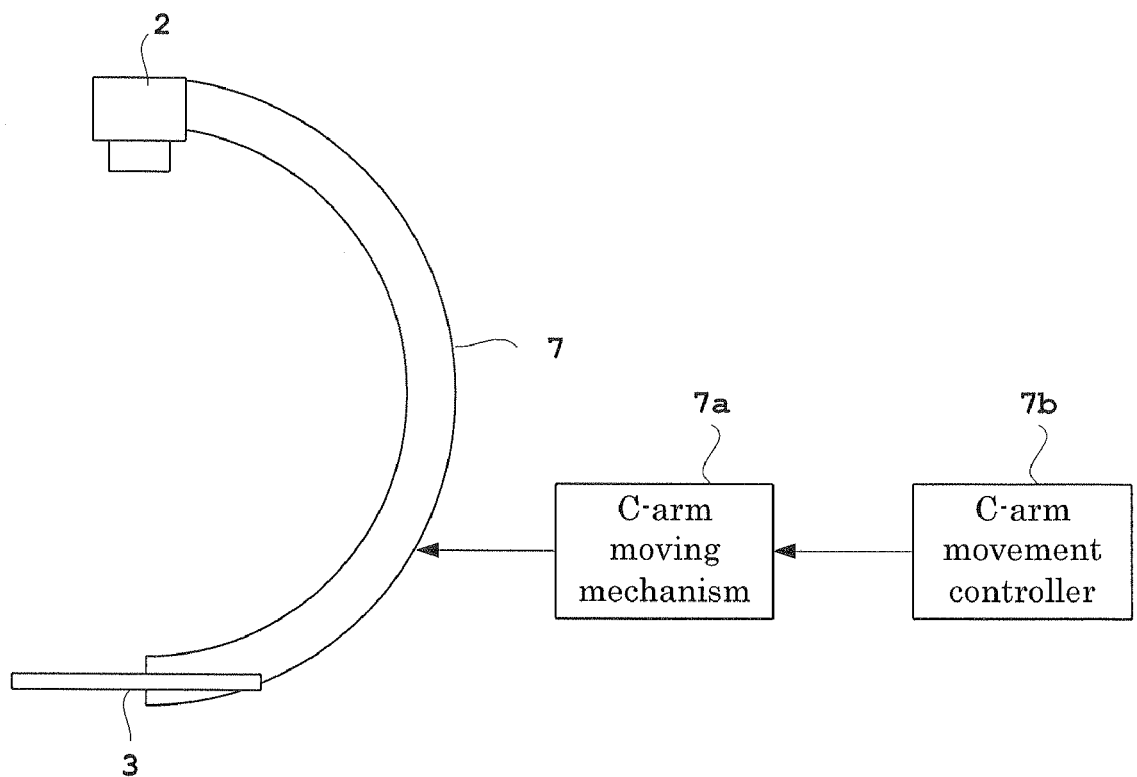
FIG. 13 is a schematic view of another modification of this invention.

(12) In the foregoing embodiment, the X-ray tube 2 and FPD 3 may be supported by a C-arm 7 as shown in FIG. 13. The C-arm 7 is arcuate, with the X-ray tube 2 mounted at one end thereof and the FPD 3 at the other end. The C-arm 7 is rotatable along an imaginary circle extending from the arc, and also rotatable about an axis perpendicular to both the central axis of the imaginary circle and a line extending between the X-ray tube 2 and FPD 3. A C-arm moving mechanism 7a causes such rotations, and a C-arm movement controller 7b controls the C-arm moving mechanism 7a.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining a radiographic image, comprising:
   a radiation source for emitting radiation;
   a radiation detecting device having a plurality of detecting elements arranged two-dimensionally in rows and columns for detecting the radiation;
   a radiation grid with absorbing foil strips extending in a direction of the rows and arranged in a direction of the columns for removing scattered radiation;
   a physical quantity acquiring device for calculating predetermined physical quantities to determine pixel values of pixels arranged two-dimensionally;
   a physical quantity map generating device for generating a physical quantity map by mapping the predetermined physical quantities; and
   a physical quantity map smoothing device for smoothing the physical quantities arranged on the physical quantity map in the direction of extension of the absorbing foil strips, thereby to generate an average value map.

2. The radiographic apparatus according to claim 1, further comprising:
   a pixel specifying device for specifying certain pixels among pixels forming the radiographic image; and
   an intensity estimating device for estimating at least one of scattered radiation intensity at the certain pixels specified by the pixel specifying device, and direct radiation intensity at the certain pixels;
   wherein
   (A) a rate of change calculating device is provided as a component corresponding to the physical quantity acquiring device, for determining a rate of change for each pixel relative to an average value or a value of each pixel obtained by smoothing and interpolating calculations as a reference intensity for the pixels relating to the radiation intensity, using the radiation intensity estimated by the intensity estimating device based on actual measurement carried out in the presence of a subject;
   (B) a rate of change map generating device is provided as a component corresponding to the physical quantity map generating device, for generating a rate of change map by mapping the rate of change for each pixel; and
   (C) a rate of change map smoothing device is provided as a component corresponding to the physical quantity map smoothing device, for smoothing rates of changes arranged on the rate of change map in the direction of extension of the absorbing foil strips, thereby to generate the average value map.

3. The radiographic apparatus according to claim 2, wherein the intensity estimating device is arranged to estimate radiation intensity at the certain pixels specified by the pixel specifying device, based on the average value map, direct radiation transmittance calculated by the transmittance calculating device, and actual measurement intensity which is a radiation intensity after transmission through the scattered radiation removing device in actual measurement carried out in the presence of a different subject.

4. The radiographic apparatus according to claim 3, wherein the physical quantity map smoothing device is arranged to remove influences of statistical noise superimposed on the physical quantity map.

5. The radiographic apparatus according to claim 4, wherein spacing between the absorbing foil strips of the radiation grid adjoining in the direction of the columns is synchronized with an integral multiple of spacing between the detecting elements of the radiation detecting device adjoining in the direction of the columns.

6. The radiographic apparatus according to claim 4, further comprising a C-arm for supporting the radiation source and the radiation detecting device.

7. The radiographic apparatus according to claim 3, wherein spacing between the absorbing foil strips of the radiation grid adjoining in the direction of the columns is synchronized with an integral multiple of spacing between the detecting elements of the radiation detecting device adjoining in the direction of the columns.

8. The radiographic apparatus according to claim 3, further comprising a C-arm for supporting the radiation source and the radiation detecting device.

9. The radiographic apparatus according to claim 2, wherein the physical quantity map smoothing device is arranged to remove influences of statistical noise superimposed on the physical quantity map.

10. The radiographic apparatus according to claim 9, wherein spacing between the absorbing foil strips of the radiation grid adjoining in the direction of the columns is synchronized with an integral multiple of spacing between the detecting elements of the radiation detecting device adjoining in the direction of the columns.

11. The radiographic apparatus according to claim 9, further comprising a C-arm for supporting the radiation source and the radiation detecting device.

12. The radiographic apparatus according to claim 2, wherein spacing between the absorbing foil strips of the radiation grid adjoining in the direction of the columns is synchronized with an integral multiple of spacing between the detecting elements of the radiation detecting device adjoining in the direction of the columns.

13. The radiographic apparatus according to claim 12, further comprising a C-arm for supporting the radiation source and the radiation detecting device.

14. The radiographic apparatus according to claim 2, further comprising a C-arm for supporting the radiation source and the radiation detecting device.

15. The radiographic apparatus according to claim 1, wherein the physical quantity map smoothing device is arranged to remove influences of statistical noise superimposed on the physical quantity map.

16. The radiographic apparatus according to claim 15, wherein spacing between the absorbing foil strips of the radiation grid adjoining in the direction of the columns is synchronized with an integral multiple of spacing between the detecting elements of the radiation detecting device adjoining in the direction of the columns.

17. The radiographic apparatus according to claim 15, further comprising a C-arm for supporting the radiation source and the radiation detecting device.

18. The radiographic apparatus according to claim 1, wherein spacing between the absorbing foil strips of the radiation grid adjoining in the direction of the columns is synchronized with an integral multiple of spacing between the detecting elements of the radiation detecting device adjoining in the direction of the columns.

19. The radiographic apparatus according to claim 18, further comprising a C-arm for supporting the radiation source and the radiation detecting device.

20. The radiographic apparatus according to claim 1, further comprising a C-arm for supporting the radiation source and the radiation detecting device.

* * * * *